(12) United States Patent
zhang et al.

(10) Patent No.: US 12,349,902 B2
(45) Date of Patent: Jul. 8, 2025

(54) POWERED HANDLE ASSEMBLY FOR SURGICAL DEVICES

(71) Applicant: Covidien LP, Mansfield, MA (US)

(72) Inventors: Zhihua zhang, Shanghai (CN); Shouwei Li, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/015,250

(22) PCT Filed: Nov. 23, 2020

(86) PCT No.: PCT/CN2020/138521
§ 371 (c)(1),
(2) Date: Jan. 9, 2023

(87) PCT Pub. No.: WO2022/007344
PCT Pub. Date: Jan. 13, 2022

(65) Prior Publication Data
US 2023/0263522 A1    Aug. 24, 2023

(30) Foreign Application Priority Data
Jul. 9, 2020    (WO) ................ PCT/CN2020/100951

(51) Int. Cl.
*A61B 17/00* (2006.01)
*A61B 17/072* (2006.01)

(52) U.S. Cl.
CPC ............... *A61B 17/07207* (2013.01); *A61B 2017/00017* (2013.01); *A61B 2017/00398* (2013.01)

(58) Field of Classification Search
CPC .... A61B 17/07207; A61B 2017/00017; A61B 2017/00398; A61B 2017/0046;
(Continued)

(56) References Cited

U.S. PATENT DOCUMENTS 3,499,591 A    3/1970    Green
3,777,538 A    12/1973   Weatherly et al.
(Continued)

FOREIGN PATENT DOCUMENTS

AU    198654765    9/1986
CA    2773414 A1    11/2012
(Continued)

OTHER PUBLICATIONS

International Search Report for Application No. PCT/CN2020/100951 dated Mar. 31, 2021.
(Continued)

*Primary Examiner* — Robert F Long

(57) ABSTRACT

A surgical device includes a powered handle assembly, an adapter assembly extending from the handle assembly, and a tool assembly that is mounted to the adapter assembly about a pivot member. The handle assembly includes a clutch that is movable between an articulation position and a clamp/fire position. In the articulation position, the handle assembly is configured to provide powered articulation of the tool assembly about the pivot member. In the clamp/fire position, the handle assembly is configured to provide actuation of the surgical device.

16 Claims, 25 Drawing Sheets

(58) Field of Classification Search
CPC .......... A61B 2017/00473; A61B 2017/07271; A61B 2017/07278
USPC ............................ 227/175.1–182.1, 8, 19
See application file for complete search history.

(56) References Cited

U.S. PATENT DOCUMENTS

| | | |
|---|---|---|
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,662,814 A * | 5/1987 | Suzuki ................... B25J 17/02 414/730 |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |

(56) References Cited

U.S. PATENT DOCUMENTS

| | | |
|---|---|---|
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |

(56) References Cited

U.S. PATENT DOCUMENTS

| | | |
|---|---|---|
| 6,592,597 B2 | 7/2003 | Grant et al. |
| 6,594,552 B1 | 7/2003 | Nowlin et al. |
| 6,602,252 B2 | 8/2003 | Mollenauer |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,021,400 B2 * | 4/2006 | Oretti ............... B23B 31/123 279/62 |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B2 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |

(56) References Cited

U.S. PATENT DOCUMENTS

| | | |
|---|---|---|
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |

(56) References Cited

U.S. PATENT DOCUMENTS

| | | |
|---|---|---|
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,405 B2 | 2/2012 | Milliman |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |

(56) References Cited

U.S. PATENT DOCUMENTS

| | | |
|---|---|---|
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czernik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |

(56) References Cited

U.S. PATENT DOCUMENTS

| | | |
|---|---|---|
| 8,573,463 B2 | 11/2013 | Scirica et al. |
| 8,573,465 B2 | 11/2013 | Shelton, IV |
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,762 B2 | 11/2013 | Hess et al. |
| 8,596,515 B2 | 12/2013 | Okoniewski |
| 8,597,311 B2 | 12/2013 | Criscuolo et al. |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek et al. |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,533 B2 | 6/2014 | Whitman |
| 8,746,534 B2 | 6/2014 | Farascioni |
| 8,746,535 B2 | 6/2014 | Shelton, IV et al. |
| 8,747,421 B2 | 6/2014 | Balbierz et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,870,050 B2 | 10/2014 | Hodgkinson |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,681 B2 | 1/2015 | Kostrzewski |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,960,520 B2 | 2/2015 | McCuen |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,991,677 B2 | 3/2015 | Moore et al. |
| 8,991,678 B2 | 3/2015 | Wellman et al. |
| 8,998,058 B2 | 4/2015 | Moore et al. |
| 8,998,060 B2 | 4/2015 | Bruewer et al. |
| 9,005,230 B2 | 4/2015 | Yates et al. |
| 9,010,606 B2 | 4/2015 | Aranyi et al. |
| 9,010,607 B2 | 4/2015 | Kostrzewski |
| 9,010,610 B2 | 4/2015 | Hodgkinson |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,544 B2 | 4/2015 | Hodgkinson et al. |
| 9,016,545 B2 | 4/2015 | Aranyi et al. |
| 9,016,546 B2 | 4/2015 | Demmy et al. |
| 9,017,371 B2 | 4/2015 | Whitman et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |

(56) References Cited

U.S. PATENT DOCUMENTS

| | | |
|---|---|---|
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | (Tarinelli) Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Lytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III et al. |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,092 B2 | 8/2017 | Baxter, III et al. |
| 9,724,095 B2 | 8/2017 | Gupta et al. |
| 9,763,662 B2 | 9/2017 | Shelton, IV et al. |
| 9,770,245 B2 | 9/2017 | Swayze et al. |
| 9,775,610 B2 | 10/2017 | Nicholas et al. |
| 9,775,635 B2 | 10/2017 | Takei |
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |

(56) References Cited

U.S. PATENT DOCUMENTS

| | | |
|---|---|---|
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter, III et al. |
| 9,855,038 B2 | 1/2018 | Smith et al. |
| 9,855,040 B2 | 1/2018 | Kostrzewski |
| 9,861,358 B2 | 1/2018 | Marczyk et al. |
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |
| 9,913,646 B2 | 3/2018 | Shelton, IV |
| 9,918,714 B2 | 3/2018 | Gibbons, Jr. |
| 9,918,717 B2 | 3/2018 | Czernik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,750 B2 | 10/2018 | Zergiebel et al. |
| 10,086,507 B2 * | 10/2018 | Hecht .................. F16C 41/001 |
| 10,092,290 B2 | 10/2018 | Yigit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,939 B2 | 7/2019 | Shelton, IV et al. |
| 10,349,941 B2 | 7/2019 | Marczyk et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,617,412 B2 | 4/2020 | Shelton, IV et al. |
| 10,624,634 B2 | 4/2020 | Shelton, IV et al. |
| 10,687,806 B2 | 6/2020 | Shelton, IV et al. |
| 10,695,053 B2 | 6/2020 | Hess et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0056756 A1 * | 3/2007 | Chung .................... B25B 21/00 173/48 |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0167159 A1 * | 7/2008 | Rapin .................... F16H 63/38 476/4 |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0289843 A1 * | 11/2008 | Townsan ............. B25B 23/0028 173/217 |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2008/0308608 A1 | 12/2008 | Prommersberger |

(56) References Cited

U.S. PATENT DOCUMENTS

| | | | |
|---|---|---|---|
| 2009/0001121 A1 | 1/2009 | Hess et al. | |
| 2009/0001129 A1* | 1/2009 | Marczyk | A61B 17/068 227/179.1 |
| 2009/0001130 A1 | 1/2009 | Hess et al. | |
| 2009/0090763 A1 | 4/2009 | Zemlok et al. | |
| 2009/0090766 A1 | 4/2009 | Knodel | |
| 2009/0098971 A1* | 4/2009 | Ho | B23B 45/008 475/281 |
| 2009/0242610 A1 | 10/2009 | Shelton, IV et al. | |
| 2009/0255974 A1 | 10/2009 | Viola | |
| 2009/0308907 A1 | 12/2009 | Nalagatla et al. | |
| 2010/0012703 A1 | 1/2010 | Calabrese et al. | |
| 2010/0065604 A1 | 3/2010 | Weng | |
| 2010/0069942 A1 | 3/2010 | Shelton, IV | |
| 2010/0127041 A1 | 5/2010 | Morgan et al. | |
| 2010/0133317 A1 | 6/2010 | Shelton, IV et al. | |
| 2010/0147921 A1 | 6/2010 | Olson | |
| 2010/0147922 A1 | 6/2010 | Olson | |
| 2010/0155453 A1 | 6/2010 | Bombard et al. | |
| 2010/0163261 A1* | 7/2010 | Tomayko | B25D 16/00 173/217 |
| 2010/0193566 A1 | 8/2010 | Scheib et al. | |
| 2010/0224668 A1 | 9/2010 | Fontayne et al. | |
| 2010/0249802 A1 | 9/2010 | May et al. | |
| 2010/0252611 A1 | 10/2010 | Ezzat et al. | |
| 2011/0006101 A1 | 1/2011 | Hall et al. | |
| 2011/0024477 A1 | 2/2011 | Hall | |
| 2011/0024478 A1 | 2/2011 | Shelton, IV | |
| 2011/0036891 A1 | 2/2011 | Zemlok et al. | |
| 2011/0062211 A1* | 3/2011 | Ross | A61B 17/00 227/175.1 |
| 2011/0087276 A1 | 4/2011 | Bedi et al. | |
| 2011/0101069 A1 | 5/2011 | Bombard et al. | |
| 2011/0147021 A1* | 6/2011 | Schaal | B25F 5/001 173/47 |
| 2011/0147433 A1 | 6/2011 | Shelton, IV et al. | |
| 2011/0163146 A1 | 7/2011 | Ortiz et al. | |
| 2011/0192882 A1 | 8/2011 | Hess et al. | |
| 2011/0278343 A1 | 11/2011 | Knodel et al. | |
| 2011/0290856 A1 | 12/2011 | Shelton, IV et al. | |
| 2012/0053406 A1 | 3/2012 | Conlon et al. | |
| 2012/0061446 A1 | 3/2012 | Knodel et al. | |
| 2012/0074200 A1 | 3/2012 | Schmid et al. | |
| 2012/0080478 A1 | 4/2012 | Morgan et al. | |
| 2012/0080495 A1 | 4/2012 | Holcomb et al. | |
| 2012/0080498 A1 | 4/2012 | Shelton, IV et al. | |
| 2012/0091183 A1 | 4/2012 | Manoux et al. | |
| 2012/0138659 A1 | 6/2012 | Marczyk et al. | |
| 2012/0193394 A1 | 8/2012 | Holcomb et al. | |
| 2012/0193399 A1 | 8/2012 | Holcomb et al. | |
| 2012/0211542 A1 | 8/2012 | Racenet | |
| 2012/0223122 A1* | 9/2012 | Roy | A61B 17/072 227/175.1 |
| 2012/0228358 A1 | 9/2012 | Zemlok et al. | |
| 2012/0234895 A1 | 9/2012 | O'Connor et al. | |
| 2012/0234897 A1 | 9/2012 | Shelton, IV et al. | |
| 2012/0241504 A1 | 9/2012 | Soltz et al. | |
| 2012/0248169 A1 | 10/2012 | Widenhouse et al. | |
| 2012/0286022 A1 | 11/2012 | Olson et al. | |
| 2012/0298722 A1 | 11/2012 | Hess et al. | |
| 2013/0008937 A1 | 1/2013 | Viola | |
| 2013/0012983 A1 | 1/2013 | Kleyman | |
| 2013/0020375 A1 | 1/2013 | Shelton, IV et al. | |
| 2013/0020376 A1 | 1/2013 | Shelton, IV et al. | |
| 2013/0026208 A1 | 1/2013 | Shelton, IV et al. | |
| 2013/0026210 A1 | 1/2013 | Shelton, IV et al. | |
| 2013/0041406 A1 | 2/2013 | Bear et al. | |
| 2013/0068816 A1 | 3/2013 | Mandakolathur Vasudevan et al. | |
| 2013/0068818 A1 | 3/2013 | Kasvikis | |
| 2013/0075447 A1 | 3/2013 | Weisenburgh, II et al. | |
| 2013/0098970 A1 | 4/2013 | Racenet et al. | |
| 2013/0123783 A1* | 5/2013 | Marczyk | A61B 18/1445 606/1 |
| 2013/0153641 A1 | 6/2013 | Shelton, IV et al. | |
| 2013/0175316 A1 | 7/2013 | Thompson et al. | |
| 2013/0256380 A1 | 10/2013 | Schmid et al. | |
| 2013/0277410 A1 | 10/2013 | Fernandez et al. | |
| 2013/0334280 A1 | 12/2013 | Krehel et al. | |
| 2014/0014704 A1 | 1/2014 | Onukuri et al. | |
| 2014/0014707 A1 | 1/2014 | Onukuri et al. | |
| 2014/0048580 A1 | 2/2014 | Merchant et al. | |
| 2014/0166724 A1 | 6/2014 | Schellin et al. | |
| 2014/0166725 A1 | 6/2014 | Schellin et al. | |
| 2014/0166726 A1 | 6/2014 | Schellin et al. | |
| 2014/0175150 A1 | 6/2014 | Shelton, IV et al. | |
| 2014/0239047 A1 | 8/2014 | Hodgkinson et al. | |
| 2014/0246475 A1 | 9/2014 | Hall et al. | |
| 2014/0252064 A1 | 9/2014 | Mozdzierz et al. | |
| 2014/0263541 A1 | 9/2014 | Leimbach et al. | |
| 2014/0263552 A1 | 9/2014 | Hall et al. | |
| 2014/0263558 A1 | 9/2014 | Hausen et al. | |
| 2014/0284371 A1 | 9/2014 | Morgan et al. | |
| 2014/0291379 A1 | 10/2014 | Schellin et al. | |
| 2014/0291383 A1 | 10/2014 | Spivey et al. | |
| 2014/0367445 A1 | 12/2014 | Ingmanson et al. | |
| 2015/0076211 A1 | 3/2015 | Irka et al. | |
| 2015/0134076 A1 | 5/2015 | Shelton, IV et al. | |
| 2015/0158168 A1* | 6/2015 | Lauterwald | B25D 16/006 173/48 |
| 2015/0173749 A1 | 6/2015 | Shelton, IV et al. | |
| 2015/0173756 A1 | 6/2015 | Baxter, III et al. | |
| 2015/0250474 A1 | 9/2015 | Abbott et al. | |
| 2015/0272557 A1 | 10/2015 | Overmyer et al. | |
| 2015/0297222 A1 | 10/2015 | Huitema et al. | |
| 2015/0297225 A1 | 10/2015 | Huitema et al. | |
| 2015/0374372 A1 | 12/2015 | Zergiebel et al. | |
| 2016/0066909 A1 | 3/2016 | Baber et al. | |
| 2016/0166249 A1 | 6/2016 | Knodel | |
| 2016/0166253 A1 | 6/2016 | Knodel | |
| 2016/0174976 A1* | 6/2016 | Morgan | A61B 17/072 227/175.1 |
| 2016/0199970 A1* | 7/2016 | McGougan | B25B 21/00 173/216 |
| 2016/0235494 A1 | 8/2016 | Shelton, IV et al. | |
| 2016/0302791 A1 | 10/2016 | Schmitt | |
| 2016/0354176 A1 | 12/2016 | Schmitt | |
| 2017/0000483 A1 | 1/2017 | Motai et al. | |
| 2017/0007339 A1* | 1/2017 | Swensgard | A61B 34/76 |
| 2017/0112561 A1 | 4/2017 | Motai | |
| 2017/0135747 A1 | 5/2017 | Broderick et al. | |
| 2017/0224334 A1 | 8/2017 | Worthington | |
| 2017/0281218 A1* | 10/2017 | Timm | A61B 17/320092 |
| 2017/0290584 A1 | 10/2017 | Jasemian et al. | |
| 2017/0296172 A1 | 10/2017 | Harris et al. | |
| 2017/0303924 A1 | 10/2017 | Scheib | |
| 2018/0008260 A1 | 1/2018 | Baxter, III et al. | |
| 2018/0055501 A1* | 3/2018 | Zemlok | A61B 17/068 |
| 2018/0168637 A1 | 6/2018 | Harris | |
| 2018/0168644 A1 | 6/2018 | Shelton, IV et al. | |
| 2018/0235610 A1 | 8/2018 | Harris et al. | |
| 2018/0325514 A1 | 11/2018 | Harris et al. | |
| 2018/0354114 A1* | 12/2018 | Bantle | B25B 21/02 |
| 2019/0099182 A1 | 4/2019 | Bakos et al. | |
| 2019/0105051 A1* | 4/2019 | Swayze | A61B 17/115 |
| 2019/0150919 A1 | 5/2019 | Williams et al. | |
| 2019/0261984 A1 | 8/2019 | Nelson et al. | |
| 2019/0298341 A1 | 10/2019 | Shelton, IV et al. | |
| 2019/0314016 A1 | 10/2019 | Huitema et al. | |
| 2019/0314019 A1 | 10/2019 | Rector et al. | |
| 2020/0054323 A1 | 2/2020 | Harris et al. | |
| 2020/0054331 A1* | 2/2020 | Harris | A61B 17/00234 |
| 2020/0121317 A1 | 4/2020 | Kostrzewski | |
| 2020/0121344 A1 | 4/2020 | Jadhav | |
| 2020/0237368 A1 | 7/2020 | Bruns et al. | |
| 2020/0261090 A1* | 8/2020 | Nicholas | A61B 17/07207 |
| 2021/0077102 A1 | 3/2021 | Williams | |
| 2022/0249182 A1* | 8/2022 | Definis | A61B 34/76 |
| 2023/0371947 A1* | 11/2023 | Shelton, IV | A61B 17/34 |

FOREIGN PATENT DOCUMENTS

| | | |
|---|---|---|
| CA | 2884962 A1 | 11/2015 |
| CN | 103989497 B | 9/2017 |

(56) References Cited

FOREIGN PATENT DOCUMENTS

| | | | |
|---|---|---|---|
| CN | 104042281 | B | 12/2017 |
| CN | 109350160 | A | 2/2019 |
| CN | 209529238 | U | 10/2019 |
| CN | 209564170 | U | 11/2019 |
| CN | 106999186 | B | 2/2020 |
| CN | 110785128 | A | 2/2020 |
| CN | 107257664 | B | 6/2020 |
| CN | 107257663 | B | 7/2020 |
| CN | 109350160 | B | 3/2021 |
| CN | 107028633 | B | 8/2021 |
| DE | 2744824 | A1 | 4/1978 |
| DE | 2903159 | A1 | 7/1980 |
| DE | 3114135 | A1 | 10/1982 |
| DE | 4213426 | A1 | 10/1992 |
| DE | 4300307 | A1 | 7/1994 |
| EP | 0041022 | A1 | 12/1981 |
| EP | 0136950 | A2 | 4/1985 |
| EP | 0140552 | A2 | 5/1985 |
| EP | 0156774 | A2 | 10/1985 |
| EP | 0213817 | A1 | 3/1987 |
| EP | 0216532 | A1 | 4/1987 |
| EP | 0220029 | A1 | 4/1987 |
| EP | 0273468 | A2 | 7/1988 |
| EP | 0324166 | A2 | 7/1989 |
| EP | 0324635 | A1 | 7/1989 |
| EP | 0324637 | A1 | 7/1989 |
| EP | 0324638 | A1 | 7/1989 |
| EP | 0365153 | A1 | 4/1990 |
| EP | 0369324 | A1 | 5/1990 |
| EP | 0373762 | A1 | 6/1990 |
| EP | 0380025 | A2 | 8/1990 |
| EP | 0399701 | A1 | 11/1990 |
| EP | 0449394 | A2 | 10/1991 |
| EP | 0484677 | A1 | 5/1992 |
| EP | 0489436 | A1 | 6/1992 |
| EP | 0503662 | A1 | 9/1992 |
| EP | 0514139 | A2 | 11/1992 |
| EP | 0536903 | A2 | 4/1993 |
| EP | 0537572 | A2 | 4/1993 |
| EP | 0539762 | A1 | 5/1993 |
| EP | 0541950 | A1 | 5/1993 |
| EP | 0545029 | A1 | 6/1993 |
| EP | 0552050 | A2 | 7/1993 |
| EP | 0552423 | A2 | 7/1993 |
| EP | 0579038 | A1 | 1/1994 |
| EP | 0589306 | A2 | 3/1994 |
| EP | 0591946 | A1 | 4/1994 |
| EP | 0592243 | A2 | 4/1994 |
| EP | 0593920 | A1 | 4/1994 |
| EP | 0598202 | A1 | 5/1994 |
| EP | 0598579 | A1 | 5/1994 |
| EP | 0600182 | A2 | 6/1994 |
| EP | 0621006 | A1 | 10/1994 |
| EP | 0621009 | A1 | 10/1994 |
| EP | 0656188 | A2 | 6/1995 |
| EP | 0666057 | A2 | 8/1995 |
| EP | 0705571 | A1 | 4/1996 |
| EP | 0760230 | A1 | 3/1997 |
| EP | 1952769 | A2 | 8/2008 |
| EP | 2090253 | A2 | 8/2009 |
| EP | 2090254 | A1 | 8/2009 |
| EP | 2583630 | A2 | 4/2013 |
| EP | 2586382 | A2 | 5/2013 |
| EP | 2907456 | A1 | 8/2015 |
| EP | 3138509 | A1 | 3/2017 |
| EP | 3338660 | A1 | 6/2018 |
| EP | 3682817 | A1 | 7/2020 |
| FR | 391239 | A | 10/1908 |
| FR | 2542188 | A1 | 9/1984 |
| FR | 2660851 | A1 | 10/1991 |
| FR | 2681775 | A1 | 4/1993 |
| GB | 1352554 | A | 5/1974 |
| GB | 1452185 | A | 10/1976 |
| GB | 1555455 | A | 11/1979 |
| GB | 2048685 | A | 12/1980 |
| GB | 2070499 | A | 9/1981 |
| GB | 2141066 | A | 12/1984 |
| GB | 2165559 | A | 4/1986 |
| JP | 51149985 | | 12/1976 |
| JP | 2001087272 | | 4/2001 |
| JP | 2010019904 | A | 1/2010 |
| JP | 2013215572 | A | 10/2013 |
| JP | 2016523116 | A | 8/2016 |
| JP | 2022530827 | A | 7/2022 |
| SU | 659146 | A1 | 4/1979 |
| SU | 728848 | A1 | 4/1980 |
| SU | 980703 | A1 | 12/1982 |
| SU | 990220 | A1 | 1/1983 |
| WO | 2008302247 | | 7/1983 |
| WO | 8910094 | A1 | 11/1989 |
| WO | 9210976 | A1 | 7/1992 |
| WO | 9308754 | A1 | 5/1993 |
| WO | 9314706 | A1 | 8/1993 |
| WO | 2004032760 | A2 | 4/2004 |
| WO | 2009071070 | A2 | 6/2009 |
| WO | 2015191887 | A1 | 12/2015 |
| WO | 2018161313 | A1 | 9/2018 |
| WO | 2019186434 | A1 | 10/2019 |

OTHER PUBLICATIONS

Written Opinion for Application No. PCT/CN2020/100951 dated Mar. 31, 2021.
International Search Report for Application No. PCT/CN2020/138521 dated Mar. 25, 2021.
Written Opinion for Application No. PCT/CN2020/138521 dated Mar. 25, 2021.
European Search Report for EP Application No. 20 94 4595 mailed Jun. 10, 2024 (11 pages).
Japense Office Action for JP Application No. 2023-501083 mailed Aug. 23, 2024 (6 pages).

* cited by examiner

POWERED HANDLE ASSEMBLY FOR SURGICAL DEVICES

FIELD

This technology is generally related to handle assemblies for surgical devices and, more particularly, to a handle assembly for a powered surgical stapling device.

BACKGROUND

Surgical devices are commonly used during surgical procedures to perform a variety of different surgical operations including stapling, grasping, cutting, and sealing tissue to name a few. Typically, a surgical device includes a handle assembly that a clinician, e.g., a surgeon, grasps to actuate the surgical device. Certain types of surgical devices perform multiple tasks and have different capabilities to allow the device to more easily access tissue within a body cavity. For example, powered surgical stapling devices include actuation buttons for approximating jaws of a tool assembly of the stapling device, for applying staples to tissue, and for cutting tissue. These stapling devices can also include knobs to facilitate articulation and/or rotation of the tool assembly in relation to the handle assembly.

Endoscopic surgical devices are used during minimally invasive surgical procedures to minimize trauma inflicted on a patient during the surgical procedure. Typically, endoscopic surgical devices include a handle assembly, an elongate body, and a tool assembly that is supported on a distal portion of the elongate body. In order to better access tissue within a body cavity during a surgical procedure, the tool assembly can be pivotably mounted to the elongate body and movable between a non-articulated position in which the tool assembly is aligned with the elongate body to articulated positions in which the tool assembly defines acute angles with the elongate body.

In order to pivot the tool assembly between the articulated and non-articulated positions, the handle assembly includes an articulation mechanism that is coupled to an articulation link positioned within the elongate body. The articulation link is movable longitudinally within the elongate body in response to actuation of the articulation mechanism to pivot the tool assembly within the body cavity.

A continuing need exists in the surgical arts for a powered handle assembly including an articulation mechanism for pivoting a tool assembly between non-articulated and articulated positions.

SUMMARY

In aspects, this disclosure relates generally to a handle assembly for a surgical device including a housing, a drive assembly, an articulation mechanism, a clutch, and a motor. The housing supports a clutch switch. The drive assembly is supported within the housing and includes a drive screw, a screw nut, and a drive rod. The drive rod has a proximal portion and a distal portion. The screw nut defines a threaded bore and includes external splines, and the drive screw extends through the threaded bore. The drive rod has a proximal portion coupled to the drive screw and a distal portion. The articulation mechanism is supported within the housing and includes a first articulation gear, a second articulation gear, and an articulation screw. The first articulation gear includes outer teeth and defines a through bore that includes splines positioned within the through bore. The second articulation gear defines a threaded bore and includes outer gear teeth that are engaged with the outer gear teeth of the first articulation gear. The clutch is supported within the housing between the first articulation gear and the screw nut and is movable between a clamp/fire position in which the clutch is engaged with the external splines of the screw nut and an articulation position in which the clutch is engaged with the splines of the first articulation gear. The motor is coupled to the clutch and is operable to rotate the clutch within the housing.

Other aspects of the disclosure are directed to a surgical device that includes a handle assembly, an adapter assembly, and a tool assembly. The handle assembly includes a housing, a drive assembly, an articulation assembly, a clutch, and a motor. The housing supports a clutch switch. The drive assembly is supported within the housing and includes a drive screw, a screw nut, and a drive rod. The drive rod has a proximal portion and a distal portion. The screw nut defines a threaded bore and includes external splines, and the drive screw extends through the threaded bore. The drive rod has a proximal portion that is coupled to the drive screw. The articulation mechanism is supported within the housing and includes a first articulation gear, a second articulation gear, and an articulation screw. The first articulation gear includes outer gear teeth and defines a through bore that includes splines that are positioned within the through bore of the first articulation gear. The second articulation gear defines a threaded bore and includes outer gear teeth that are engaged with the outer gear teeth of the first articulation gear. The clutch is supported within the housing between the first articulation gear and the screw nut and is movable between a clamp/fire position in which the clutch is engaged with the external splines of the screw nut and an articulation position in which the clutch is engaged with the splines of the first articulation gear. The motor is coupled to the clutch and is operable to rotate the clutch within the housing. The adapter assembly defines a longitudinal axis, has a proximal portion and a distal portion, and includes an articulation rod. The proximal portion of the adapter assembly is coupled to the handle assembly. The articulation rod has a proximal portion that is coupled to the articulation screw and a distal portion. The drive rod extends through the adapter assembly. The tool assembly is pivotably coupled to the distal portion of the adapter assembly about an axis that is transverse to the longitudinal axis of the adapter assembly. The distal portion of the articulation rod is coupled to the tool assembly such that longitudinal movement of the articulation screw pivots the tool assembly between a non-articulated position in which the tool assembly is aligned with the longitudinal axis and articulated positions in which the tool assembly is misaligned with the longitudinal axis.

In aspects of the disclosure, a first bevel gear is coupled to the motor and a second bevel gear coupled to the first bevel gear.

In some aspects of the disclosure, the second bevel gear defines a through bore and a longitudinal slot that communicates with the through bore.

In certain aspects of the disclosure, the through bore of the second bevel gear receives the screw nut and the drive screw, and the clutch includes a raised extension that is received within the longitudinal slot to rotatably couple the clutch to the second bevel gear.

In aspects of the disclosure, the articulation mechanism includes an articulation link that is coupled to the articulation screw such that longitudinal movement of the articulation screw causes longitudinal movement of the articulation link.

In some aspects of the disclosure, a clutch switch is supported on the housing and is coupled to the clutch and movable along the housing to move the clutch between the articulation position and the clamp/fire position.

In aspects of the disclosure, the clutch switch is coupled to the clutch by a forked member that includes spaced tines.

In some aspects of the disclosure, the clutch defines an annular channel and the tines of the forked member are received in the annular channel.

In certain aspects of the disclosure, an actuation button is supported on the housing, a printed circuit board is supported within the housing, and the actuation button is coupled to the motor via the printed circuit board.

In aspects of the disclosure, a battery is supported within the housing.

In some aspects of the disclosure, a manual retraction mechanism is secured to the drive screw and is rotatable to rotate the drive screw.

In certain aspects of the disclosure, the manual retraction mechanism includes a tubular body portion that receives the drive screw and a handle that is coupled to the tubular body portion and extends from a proximal portion of the housing.

In aspects of the disclosure, the housing includes a proximal cover portion that encloses the handle of the manual retraction mechanism.

In aspects of the disclosure, the tool assembly includes a stapling device having an anvil assembly and a cartridge assembly, and the anvil assembly is coupled to the cartridge assembly such that the tool assembly is movable between an open position and a clamped position.

Still other aspects of the disclosure are directed to a handle assembly for a surgical device that includes a body, a drive assembly, an articulation mechanism, a clutch, a biasing member, and a motor. The body supports at least one clutch switch. The drive assembly is supported within the housing and includes a drive screw, a screw nut, and a drive rod. The drive rod has a proximal portion and a distal portion. The screw nut defines a threaded bore and includes external splines. The drive screw extends through the threaded bore, and the drive rod has a proximal portion that is coupled to the drive screw. The articulation mechanism is supported within the housing and includes a first articulation gear, a second articulation gear, and an articulation screw. The first articulation gear defines a through bore and includes splines positioned within the through bore and outer gear teeth. The second articulation gear includes outer gear teeth that are engaged with the outer gear teeth of the first articulation gear. The clutch is supported within the housing between the first articulation gear and the screw nut. The clutch is movable between a clamp/fire position in which the clutch is engaged with the external splines of the screw nut and an articulation position in which the clutch is engaged with the splines of the first articulation gear. The biasing member is supported within the housing and urges the clutch towards the clamp/fire position. The motor is coupled to the clutch and is operable to rotate the clutch within the housing to actuate one of the drive assembly or the articulation mechanism.

Still other aspects of the disclosure are directed to a surgical device including a handle assembly, an adapter assembly, and a tool assembly. The handle assembly includes a body, a drive assembly, an articulation mechanism, a clutch, a biasing member, and a motor. The body supports at least one clutch switch. The drive assembly is supported within the housing and includes a drive screw, a screw nut, and a drive rod. The drive rod has a proximal portion and a distal portion. The screw nut defines a threaded bore and includes external splines. The drive screw extends through the threaded bore. The drive rod has a proximal portion that is coupled to the drive screw. The articulation mechanism is supported within the housing and includes a first articulation gear, a second articulation gear, and an articulation screw. The first articulation gear defines a through bore and includes splines that are positioned within the through bore and outer gear teeth. The second articulation gear includes outer gear teeth that are engaged with the outer gear teeth of the first articulation gear. The clutch is supported within the housing between the first articulation gear and the screw nut. The clutch is movable between a clamp/fire position in which the clutch is engaged with the external splines of the screw nut and an articulation position in which the clutch is engaged with the splines of the first articulation gear. The biasing member is supported within the housing and is positioned to urge the clutch towards the clamp/fire position. The motor is coupled to the clutch and is operable to rotate the clutch within the housing. The adapter assembly defines a longitudinal axis and has a proximal portion and a distal portion. The adapter assembly includes an articulation rod. The proximal portion of the adapter assembly is coupled to the handle assembly and the articulation rod has a proximal portion that is coupled to the articulation screw and a distal portion. The drive rod extends through the adapter assembly. The tool assembly is pivotably coupled to the distal portion of the adapter assembly about an axis that is transverse to the longitudinal axis of the adapter assembly. The distal portion of the articulation rod is coupled to the tool assembly to pivot the tool assembly between a non-articulated position in which the tool assembly is aligned with the longitudinal axis and articulated positions in which the tool assembly is misaligned with the longitudinal axis.

In aspects of the disclosure, the at least one clutch switch includes a clutch switch positioned on each side of the body.

In some aspects of the disclosure, the clutch switches are coupled to the clutch by forked members, and the clutch switches are movable along the body to move the clutch from the clamp/fire position to the articulation position.

In certain aspects of the disclosure, the body supports guide rods and the forked members define openings.

In aspects of the disclosure, the guide rods extend through the openings in the forked members to guide movement of the forked members as the clutch is moved from the clamp/fire position to the articulation position.

In some aspects of the disclosure, the handle assembly includes a safety toggle mechanism that is supported on the body and includes at least one toggle member and a shaft coupled to the at least one toggle member that is rotatable in response to manipulation of the at least one toggle member to move the safety toggle mechanism from an inactive position in which the handle assembly is deactivated to an active position in which the handle assembly is activated.

In certain aspects of the disclosure, the body of the handle assembly supports a contact and the shaft of the safety toggle mechanism includes an arm.

In aspects of the disclosure, in the inactive position of the safety toggle mechanism, the arm is spaced from the contact and the contact is in an open position, and in the active position of the safety toggle mechanism, the arm is engaged with the contact and the contact is in a closed position.

In some aspects of the disclosure, the safety toggle mechanism includes a slider that is mounted on the shaft and includes a stop member.

In certain aspects of the disclosure, the drive assembly includes a coupling member that couples the drive screw to the drive rod.

In aspects of the disclosure, when the clutch is in the clamp/fire position, the drive screw, the coupling member and the drive rod are movable between retracted and advanced positions within the body in response to actuation of the motor.

In some aspects of the disclosure, the coupling member is positioned to obstruct movement of the safety toggle mechanism from the inactive position to the active position when the coupling member is in its retracted position.

In certain aspects of the disclosure, the body supports a tapered cam member that has a tapered cam surface and proximal stop surface, and the slider includes a projection.

In aspects of the disclosure, the projection is movable along the tapered cam surface to move the slider from a first position on the shaft in which the slider is aligned with the tapered cam member to a second position on the shaft in which the slider is positioned outwardly of the tapered cam member as the safety toggle mechanism is moved from the inactive position to the active position.

In some aspects of the disclosure, the projection is aligned with the proximal stop surface when the safety toggle mechanism is in the active position to retain the safety toggle mechanism in the active position.

In certain aspects of the disclosure, the slider is urged towards the first position by a biasing mechanism.

Other features of the disclosure will be appreciated from the following description.

BRIEF DESCRIPTION OF DRAWINGS

Various aspects of a surgical device including a handle assembly according to aspects of the disclosure are described herein below with reference to the drawings, wherein.

DETAILED DESCRIPTION

Figure 1:
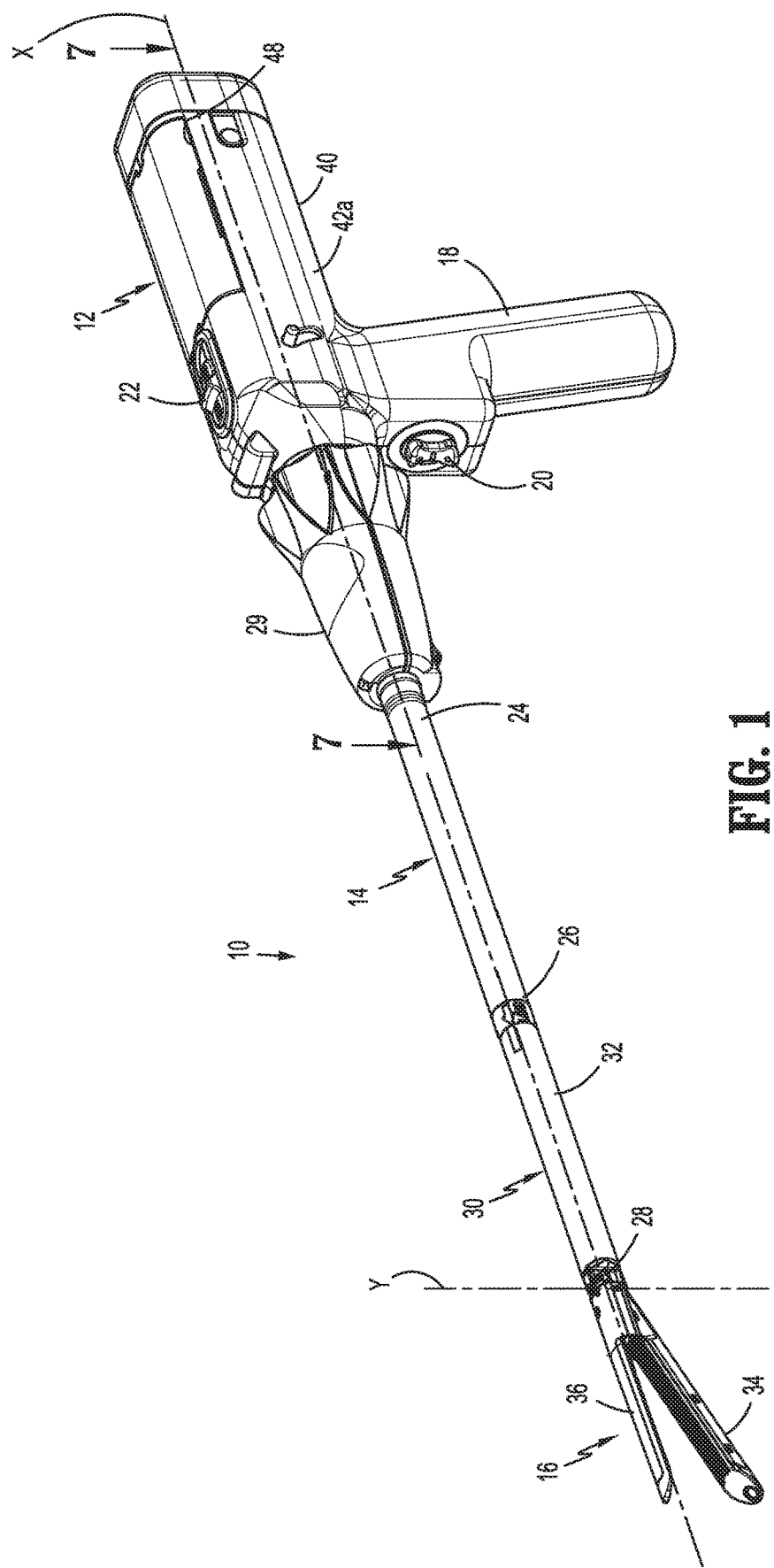
FIG. 1 is a side perspective view from a distal end of the disclosed powered surgical device with a tool assembly in a non-articulated position.
Figure 2:
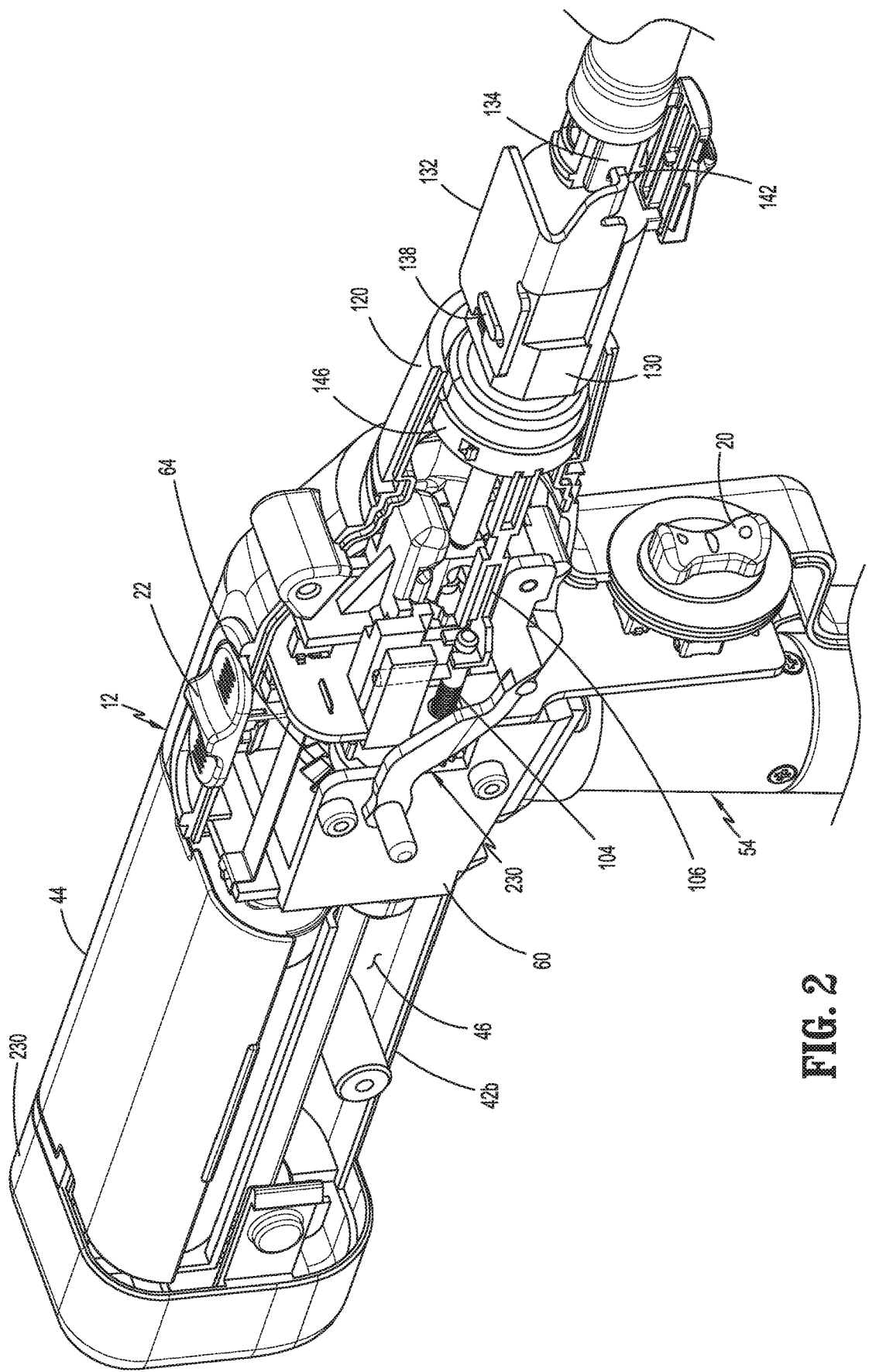
FIG. 2 is a side perspective view of a handle assembly of the surgical device shown in FIG. 1 with a housing half-section removed and a clutch in an articulation position.
Figure 3:
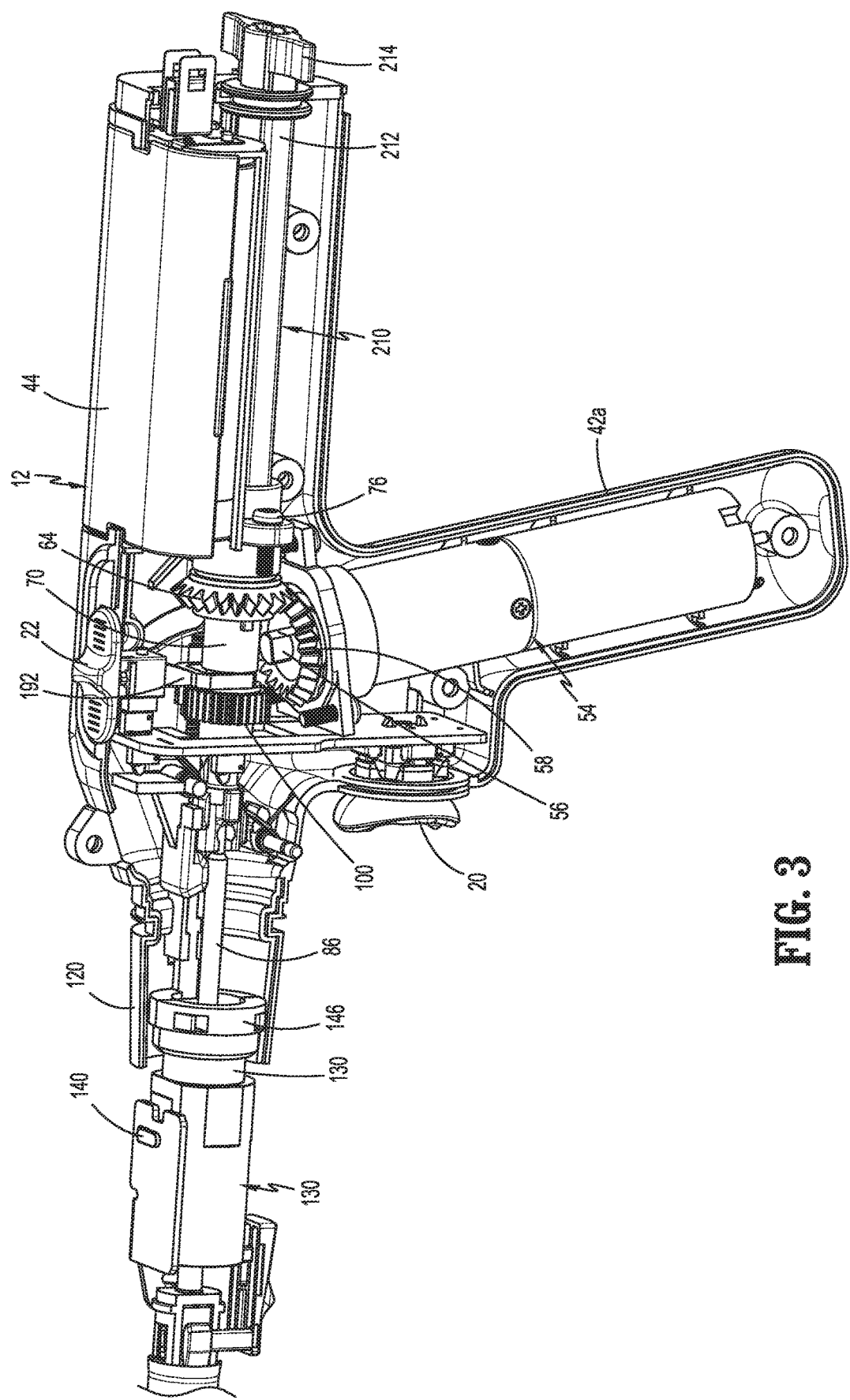
FIG. 3 is a side perspective view of the handle assembly shown in FIG. 2 with the other housing half-section removed and the clutch in the articulation position.
Figure 4:
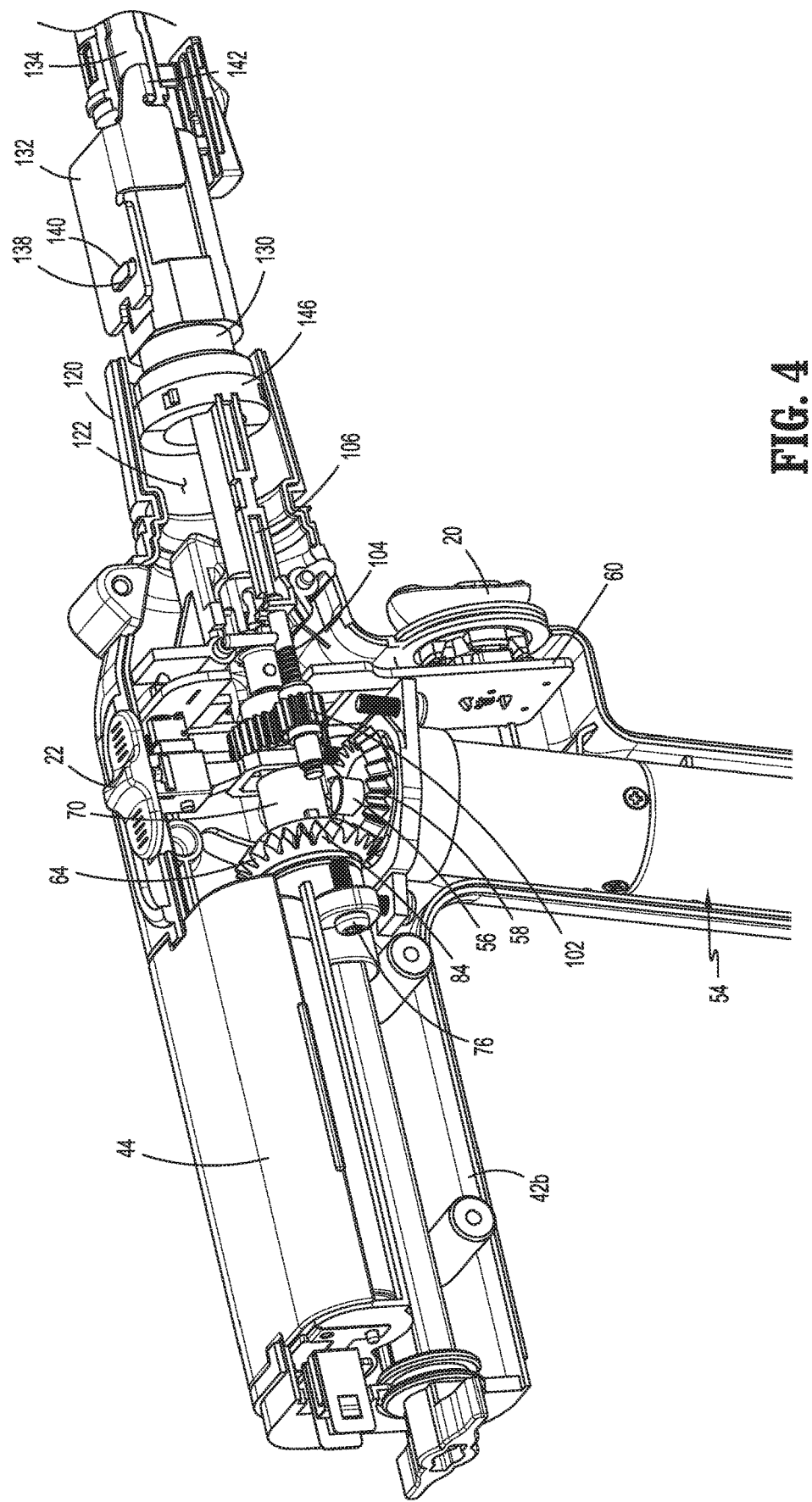
FIG. 4 is a side perspective view of the handle assembly shown in FIG. 2 with the housing half-section removed and the clutch in the articulation position.

The disclosed surgical device will now be described in detail with reference to the drawings in which like reference numerals designate identical or corresponding elements in each of the several views. However, it is to be understood that the aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure. In addition, directional terms such as front, rear, upper, lower, top, bottom, distal, proximal, and similar terms are used to assist in understanding the description and are not intended to limit the disclosure.

In this description, the term "proximal" is used generally to refer to that portion of the device that is closer to a clinician, while the term "distal" is used generally to refer to that portion of the device that is farther from the clinician. In addition, the term "endoscopic" is used generally to refer to endoscopic, laparoscopic, arthroscopic, and/or any other procedure conducted through a small diameter incision or cannula. Further, the term "clinician" is used generally to refer to medical personnel including doctors, nurses, and support personnel.

This disclosure is directed to a surgical device that includes a powered handle assembly, an adapter assembly extending from the handle assembly, and a tool assembly that is mounted to the adapter assembly about a pivot member. The handle assembly includes a clutch that is movable between an articulation position and a clamp/fire position. In the articulation position, the handle assembly is configured to provide powered articulation of the tool assembly about the pivot member. In the clamp/fire position, the handle assembly is configured to provide actuation of the surgical device.

FIG. 1 illustrates a surgical device shown generally as stapling device 10 which includes a handle assembly 12, an elongate body or adapter assembly 14, and a tool assembly 16. The handle assembly 12 includes a stationary handle portion 18, an actuation button 20, and a clutch switch 22. The adapter assembly 14 defines a longitudinal axis "X" and includes a proximal portion 24 that is coupled to the handle assembly 12, and a distal portion 26 that supports the tool assembly 16. The tool assembly 16 is secured to the distal portion 26 of the adapter assembly 14 by a pivot member 28 that defines an axis "Y" that is transverse to the longitudinal axis "X". The tool assembly 16 can articulate about the axis "Y" between an articulated position in which the tool assembly 16 is aligned with the longitudinal axis "Y" and non-articulated positions in which a longitudinal axis of the tool assembly and the longitudinal axis "X" define acute angles. The adapter assembly 14 is supported within a rotation knob 29 that is rotatably coupled to a distal portion of the handle assembly 12. The rotation knob 29 is manually rotatable about the longitudinal axis "X" to rotate the adapter assembly 14 and the tool assembly 16 about the longitudinal axis "X".

In aspects of the disclosure, the tool assembly 16 forms part of a reload assembly 30 that includes a proximal body portion 32 and is releasably coupled to the distal portion of the adapter assembly 14. The reload assembly 30 can be removed from the adapter assembly 14 and replaced to facilitate reuse of the adapter assembly 14 and handle assembly 12. Alternately, the tool assembly 16 can be secured directly to the distal portion 26 of the adapter assembly 14.

As illustrated, the tool assembly 16 can be a stapling device and include a cartridge assembly 34 and an anvil 36 that are movable in relation to each other between an open position and a clamped position. In aspects of the disclosure, the anvil 36 is fixedly secured to the proximal body portion 32 of the reload assembly 30 and the cartridge assembly can pivot between the open and clamped positions. It is envisioned that the cartridge assembly 34 can be fixedly mounted to the proximal body portion 32 and the anvil 36 can pivot between the open and clamped positions. Although the tool assembly 16 is illustrated as a stapling device, it is envisioned that the tool assembly 16 may include a variety of different types of surgical devices including graspers, vessel sealers, clip appliers, stitching devices or the like.

FIGS. 2-5 illustrate the handle assembly 12 of the stapling device 10 which includes a housing 40 (FIG. 1) formed of first and second half-sections 42a and 42b and a battery pack 44. The first and second half-sections 42a and 42b are coupled together to form the stationary handle portion 18 (FIG. 1) and define a cavity 46 having an opening 48 (FIG. 1). The battery pack 44 is received and secured within the opening 48 and includes a base portion 50 (FIG. 5) that includes electrical contacts 52.

The stationary handle portion 18 of the housing 40 of the handle assembly 12 supports a motor 54 that includes a motor shaft 56. The motor shaft 56 is secured to a first bevel gear 58 such that when the motor 54 is energized, the motor shaft 56 rotates the first bevel gear 58. The handle assembly 12 includes a gear housing 60 that is secured above the stationary handle portion 18 of the housing 40 of the handle assembly 12 with, e.g., screws 61 (FIG. 5) such that the first bevel gear 58 is positioned within the gear housing 60. The gear housing 60 supports a printed circuit board 62 ("PCB") which is electrically coupled to the actuation button 20 and to the battery pack 44.

Figure 5:
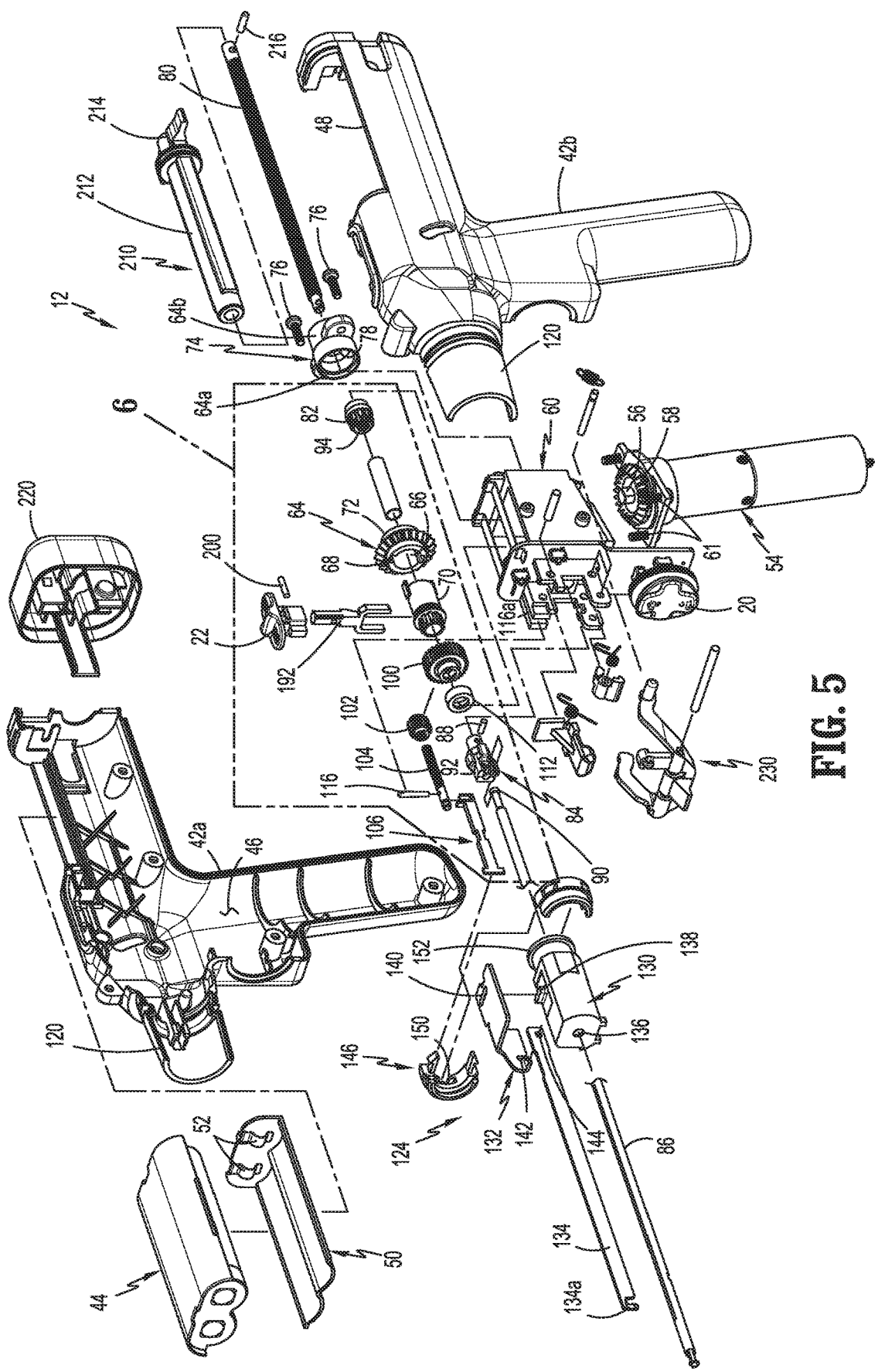
FIG. 5 is a side perspective, exploded view of the handle assembly shown in FIG. 2.

The handle assembly 12 includes a second bevel gear 64 that is engaged with the first bevel gear 58 and is positioned within the gear housing 60. The second bevel gear 64 defines a central through bore 66 (FIG. 5). The central through bore 66 includes longitudinal slots 68 that extend along a length of the central through bore 66. The longitudinal slots 68 are provided to couple the second bevel gear 64 to a clutch 70 as described in further detail below. The second bevel gear 64 is coupled to the first bevel gear 58 such that rotation of the first bevel gear 58 about a first axis causes rotation of the second bevel gear 64 about a second axis that is substantially transverse to the first axis.

Figure 7:
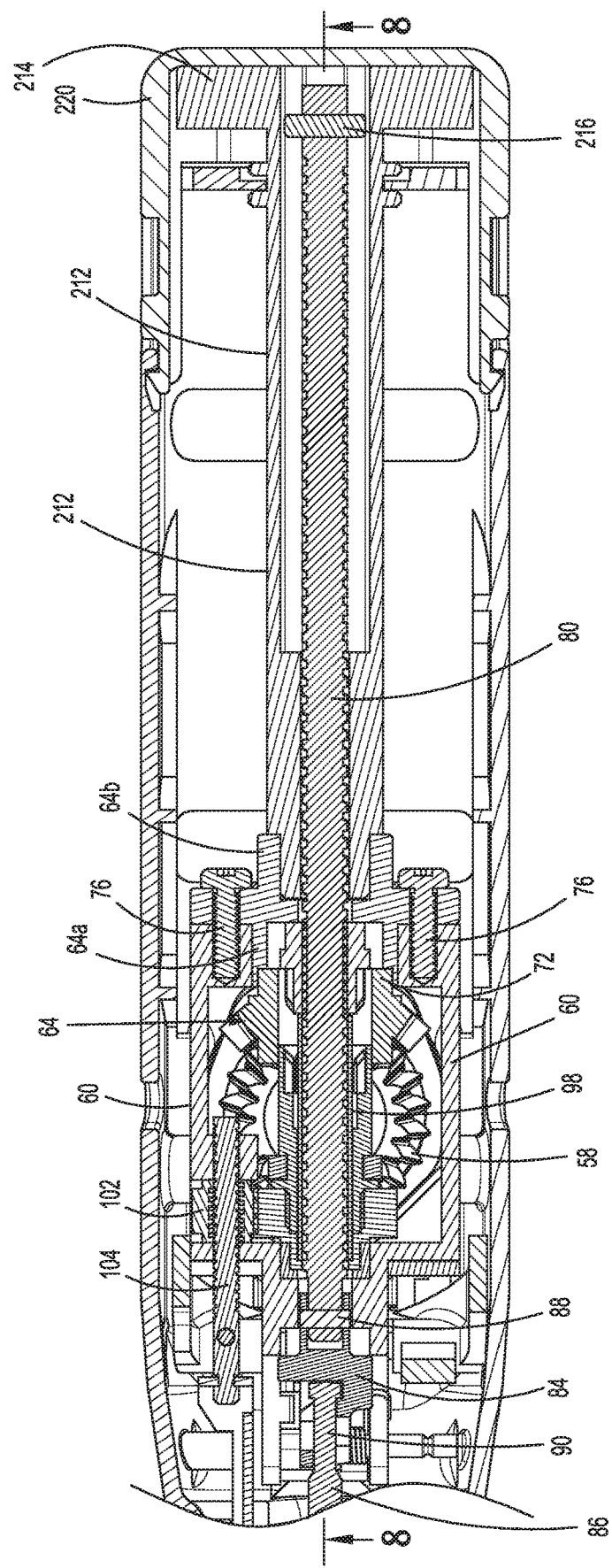
FIG. 7 is a cross-sectional view taken along section line 7-7 of FIG. 1.

The handle assembly 12 includes a support member 74 that has a distal annular flange 64a (FIG. 7) and a proximal annular flange 64b (FIG. 7). The second bevel gear 64 includes a proximal hub portion 72 that is supported for rotation within the distal annular flange 64a. In aspects of the disclosure, the support member 74 is fixedly secured to the gear housing 60 within the housing 40 of the handle assembly 12 by screws 76 (FIG. 5). The support member 74 defines a through bore 78 that extends between the annular flanges 64a and 64b of the support member 74 (FIG. 7).

Figure 6:
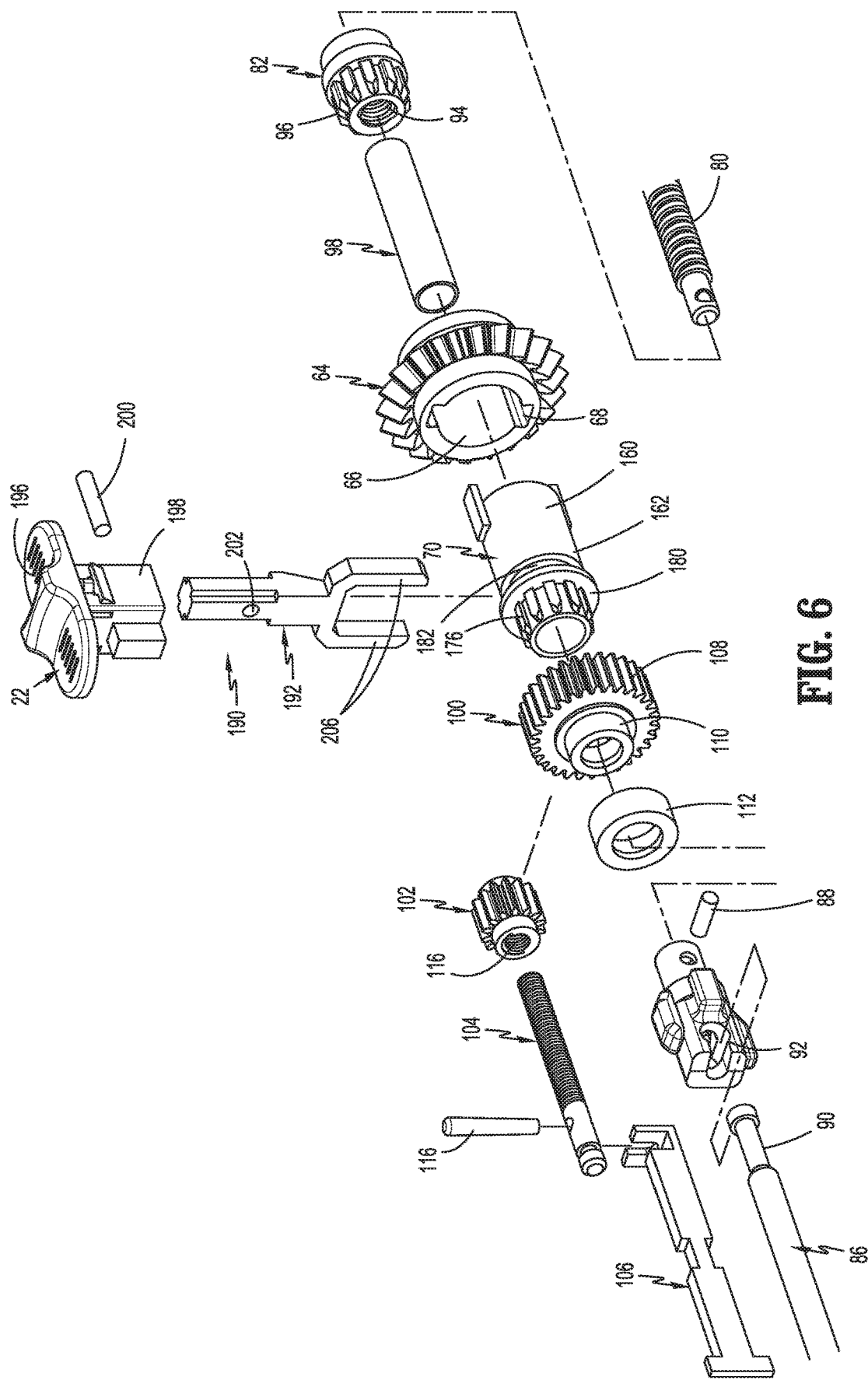
FIG. 6 is an enlarged view of the indicated area of detail shown in FIG. 5.

FIGS. 5-7 illustrate components of a drive assembly of the handle assembly 12. The drive assembly includes a drive screw 80, a screw nut 82, a coupling member 84, and a drive rod 86. The drive screw 80 extends through the through bore 78 of the support member 74 and has a proximal portion and a distal portion. The distal portion of the drive screw 80 is fixedly coupled to a proximal portion of the coupling member 84 by a pin 88 (FIG. 5). The coupling member 84 includes a distal portion that is coupled to a proximal portion of the drive rod 86. In aspects of the disclosure, the proximal portion of the drive rod 86 includes a stepped portion 90 that is received within a slot 92 (FIG. 6) in the distal portion of the coupling member 84 to axially fix the drive rod 86 to the coupling member 84 but allow the drive rod 86 to rotate in relation to the coupling member 84. The components on the drive assembly are coupled such that the longitudinal movement of the drive screw 80 causes longitudinal movement of the drive rod 86.

The screw nut 82 is received partly within the central through bore 66 of the second bevel gear 64 and within the distal annular flange 64a of the support member 64. The screw nut 82 defines a threaded through bore 94 and includes external gear teeth or splines 96 (FIG. 6). The threaded through bore 94 receives the drive screw 80 to threadedly couple the screw nut 82 about the drive screw 80. The splines 96 engage the clutch 70 when the clutch 70 is in a clamp/fire position as described in further detail below.

A tubular spacer 98 is received about the drive screw 80 and engages a distal portion of the screw nut 82 to maintain the axial position of the screw nut 82 within the housing 40 of the handle assembly 12. The tubular spacer 98 also supports the clutch 70 for movement between the clamp/fire position and an articulation position as described in further detail below.

Figure 8:
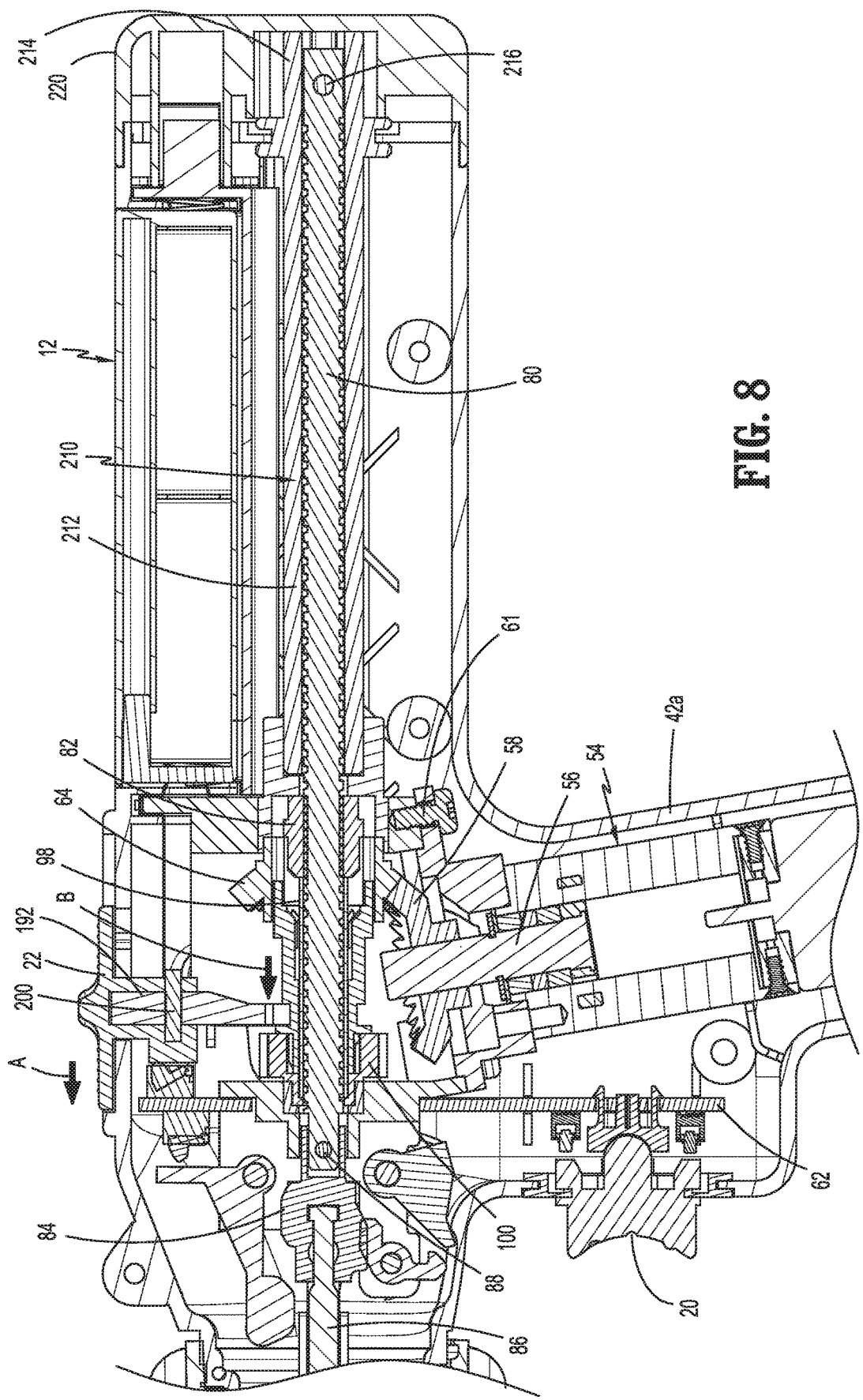
FIG. 8 is a cross-sectional view taken along section line 8-8 of FIG. 7.

The handle assembly 12 includes an articulation mechanism that includes a first articulation gear 100, a second articulation gear 102, an articulation screw 104, and an articulation link 106. The first articulation gear 100 is supported for rotation on the gear housing 60 and includes outer gear teeth 108. In aspects of the disclosure, the first articulation gear 100 includes a distally extending hub (FIG. 6) that is rotatably supported on a bearing 112 supported on the gear housing 60. The first articulation gear 100 and the bearing 112 define central openings that receive the drive screw 80. The central opening of the first articulation gear 100 is defined by an annular array of splines 114 (FIG. 13) that are engaged by the clutch 70 when the clutch 70 is moved to the articulation position (FIG. 8)

The second articulation gear 102 is rotatably supported on the gear housing 60 and is engaged with the first articulation gear 100. The second articulation gear 102 defines a threaded through bore 116 that receives the articulation screw 104. The second articulation gear 102 is axially fixed to the gear housing 60 such rotation of the second articulation gear 102 causes longitudinal movement of the articulation screw 104. The articulation screw 104 includes a distal portion that is coupled to a proximal portion of the articulation link 106 such that longitudinal movement of the articulation screw 104 causes longitudinal movement of the articulation link 106. In some aspects of the disclosure, the articulation screw 104 includes a guide pin 116 that extends along an axis that is transverse to the longitudinal axis "X" (FIG. 1). The guide pin 116 is received within a channel 116a defined in the gear housing 60 of the handle assembly 12 to prevent the articulation screw 104 from rotating within the housing 40 of the handle assembly 12.

The distal portion of the housing 40 of the handle assembly 12 includes a barrel portion 120 that defines a cavity 122 that receives an articulation linkage 124 (FIG. 5) that includes an articulation body 130, an articulation frame 132, and an articulation rod 134. The articulation body 130 defines a through bore 136 (FIG. 5) that receives the drive rod 86 and includes a protrusion 138. The articulation frame 132 includes body defining an opening 140 that receives the protrusion 138 to fixedly secure the articulation frame 132 to the articulation body 130. The articulation frame 132 includes a finger 142 that is received within an opening 144 (FIG. 5) in a proximal portion of the articulation rod 134 to couple the articulation frame 132 to the articulation rod 134. The articulation rod 134 includes a hooked portion 134a at is distal end that is configured to engage an articulation link (not shown) included in the reload assembly 30 (FIG. 1) to facilitate articulation of the tool assembly 16 upon longitudinal movement of the articulation rod 134. U.S. Pat. No. 10,123,799 discloses exemplary aspects of a surgical device including a tool assembly that is mounted for articulation and is adapted to releasably engage an articulation rod of a surgical device.

The articulation linkage 124 also includes a two-part clip 146 that secures the articulation link 106 to the articulation body 130. In aspects of the disclosure, the articulation link 106 has a T-shaped head portion that is received within a T-shaped slot 150 defined in one of the pieces of the two-part clip. The two-part clip 146 is secured about an annular flange 152 formed on a proximal portion of the articulation body 130 to rotatably couple the articulation body 130 to the articulation link 106. This arrangement allows the articulation body 130 to rotate in relation to the articulation link 106, such as when the rotation knob 29 (FIG. 1) is rotated in relation to the handle assembly 12, to facilitate rotation of the adapter assembly 14 and tool assembly 16 about the longitudinal axis "X".

Figure 15:
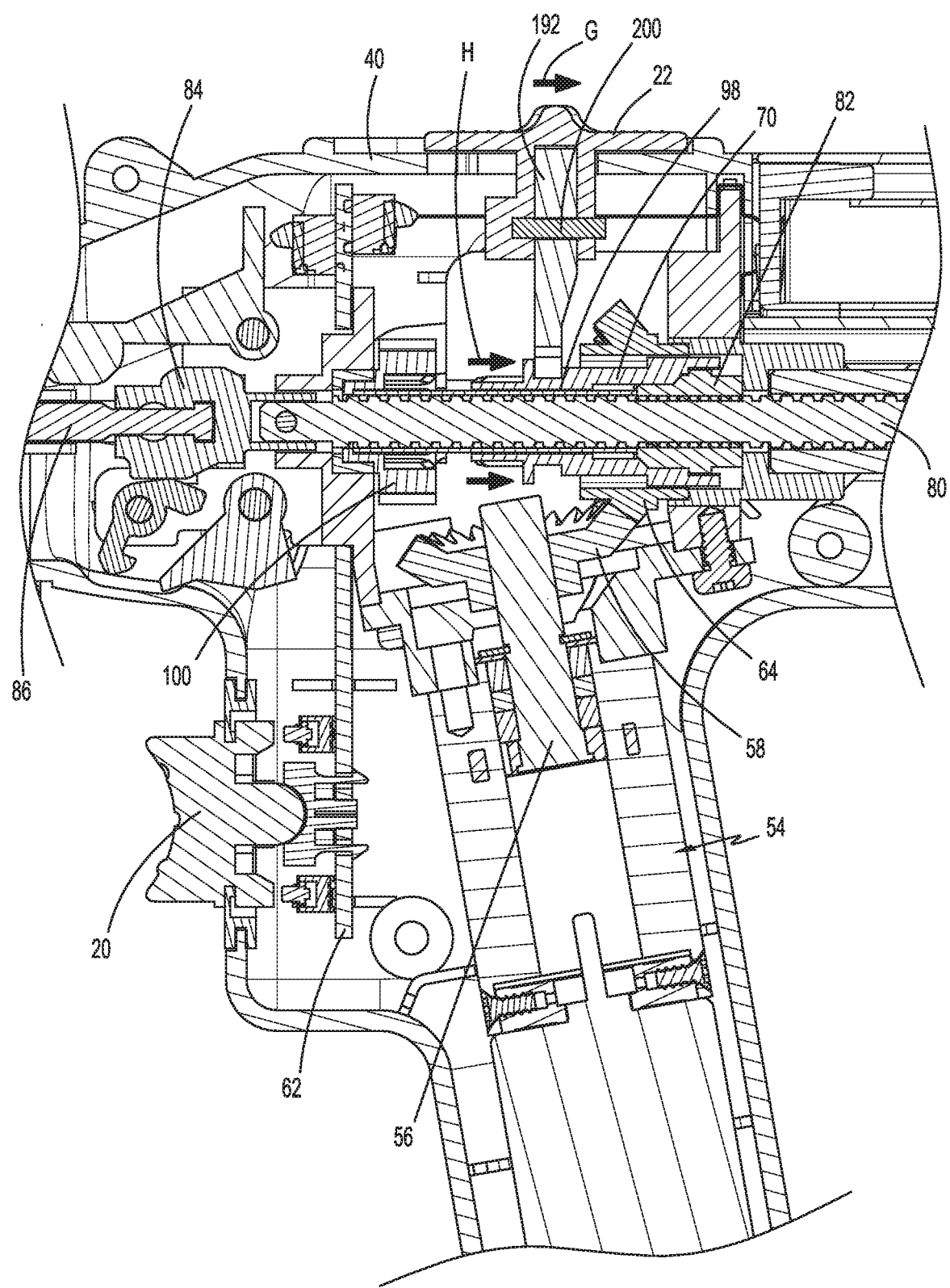
FIG. 15 is a side cross-sectional view of the handle assembly shown in FIG. 8 with the clutch in the clamp/fire position and the handle assembly actuated to move a drive rod of the handle assembly proximally.
Figure 16:
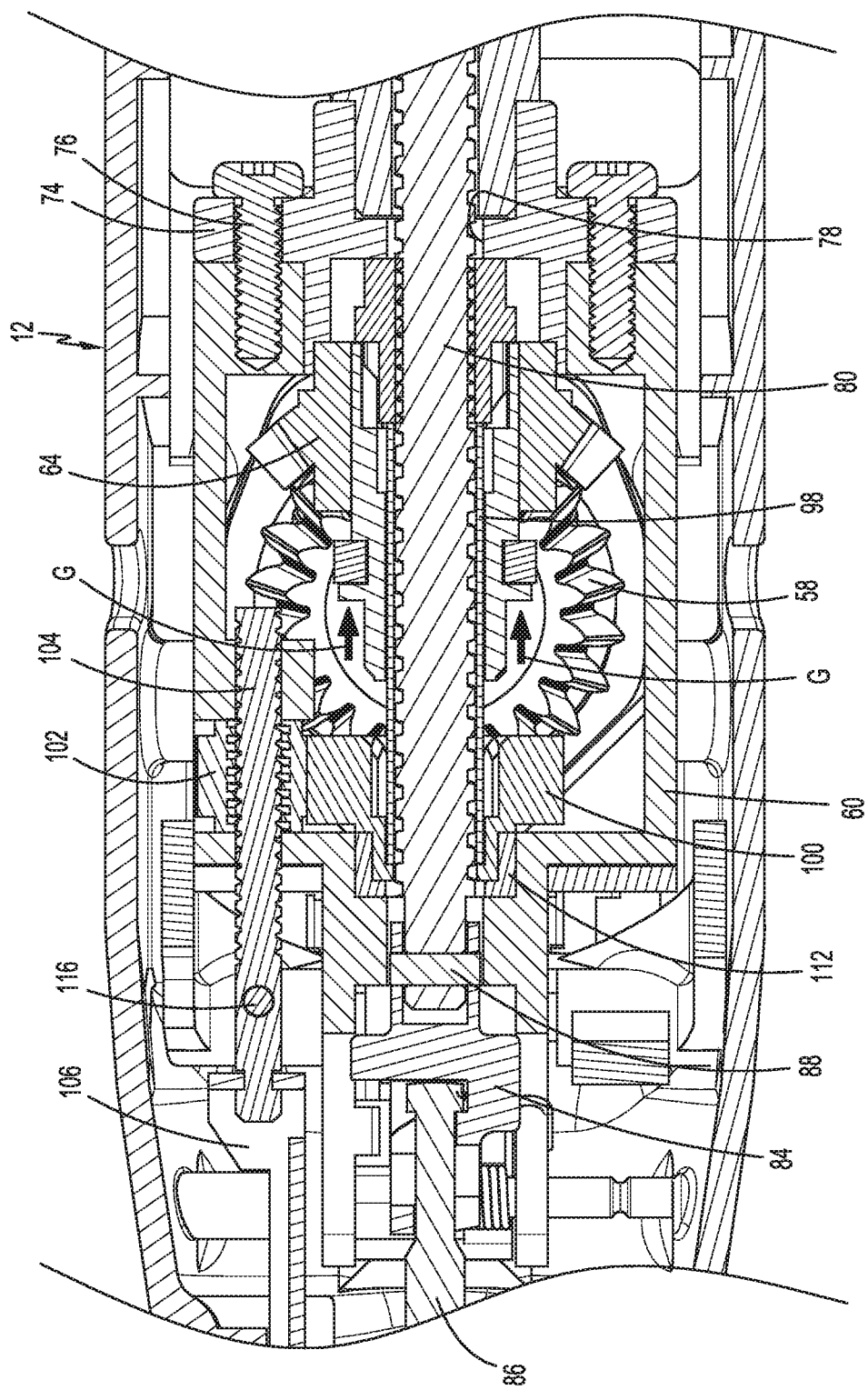
FIG. 16 is a cross-sectional view of the handle assembly shown in FIG. 15 with the clutch in the clamp/fire position and the handle assembly actuated to move the drive rod of the handle assembly proximally.
Figure 17:
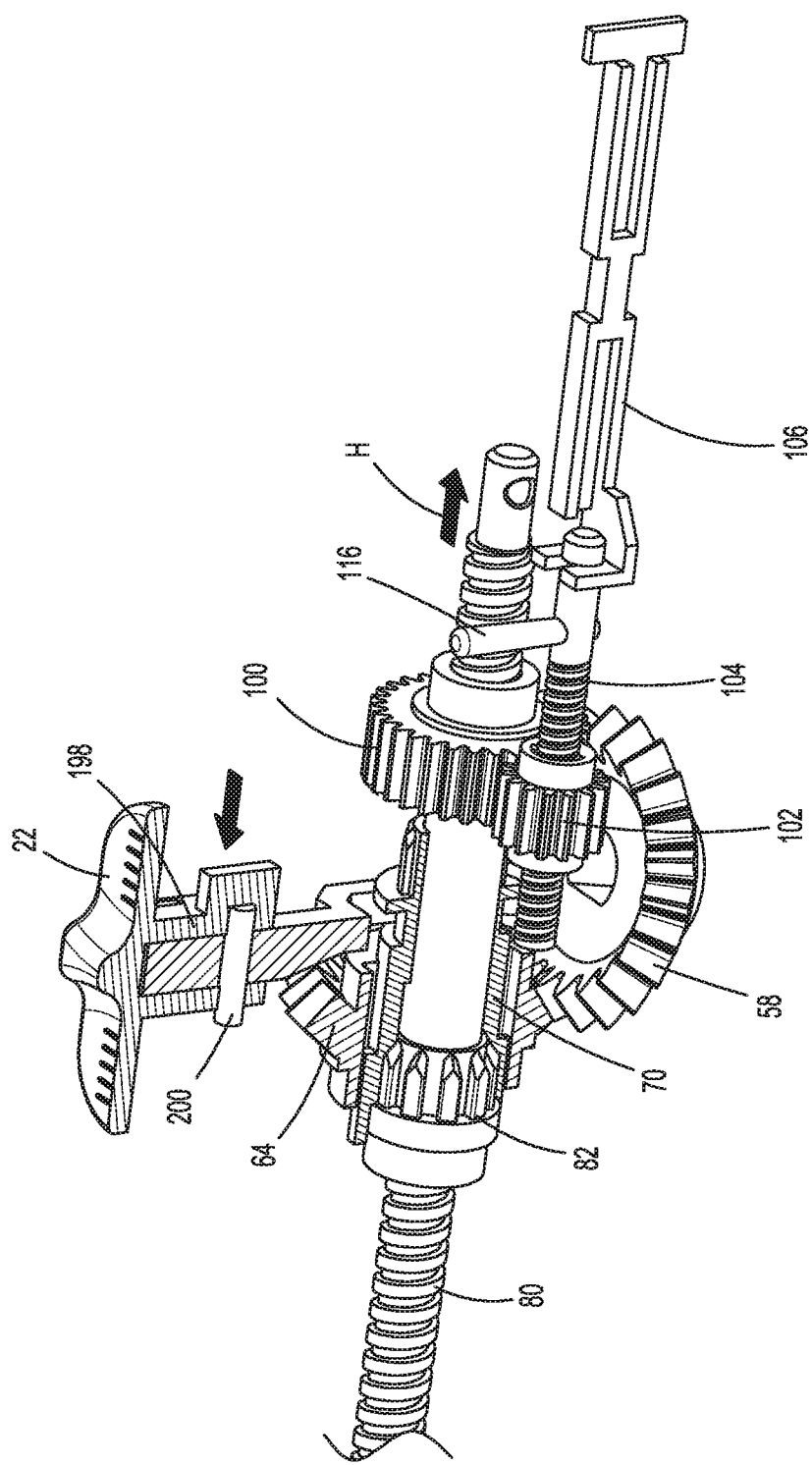
FIG. 17 is a side perspective view of the drive assembly and clutch of the handle assembly shown in FIG. 15 with the clutch in the clamp/fire position and the handle assembly actuated to move the drive rod of the handle assembly proximally.
Figure 18:
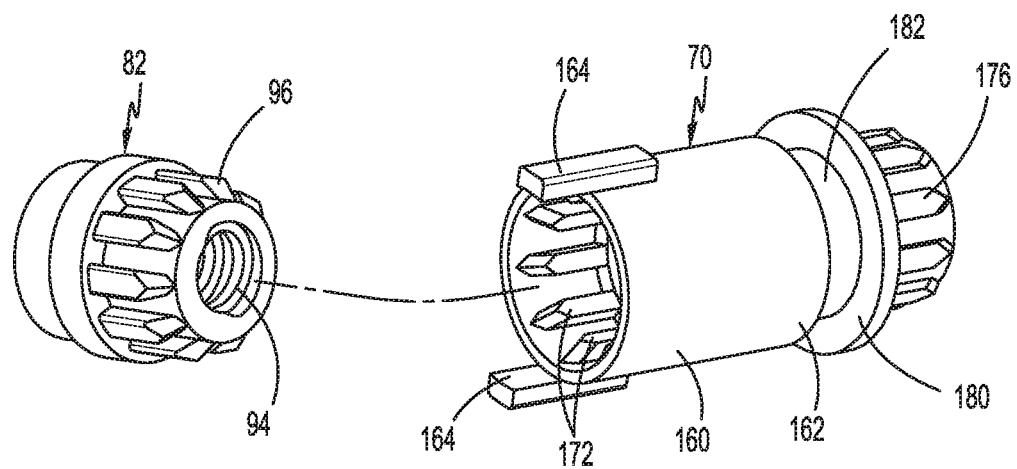
FIG. 18 is a side perspective view of the clutch and screw nut of the drive assembly shown in FIG. 17 with the parts separated.
Figure 19:
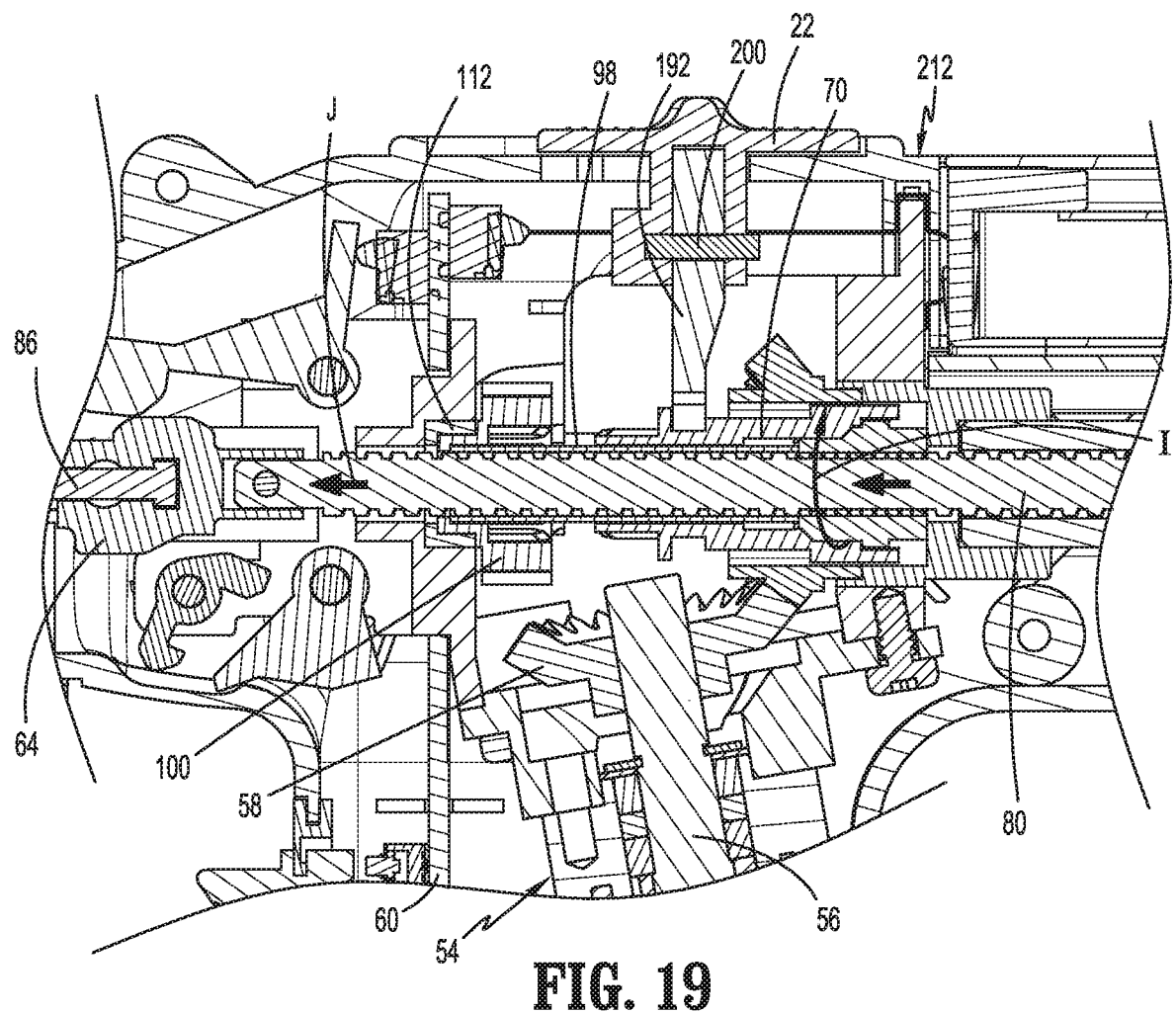
FIG. 19 is a side cross-sectional view of the handle assembly shown in FIG. 15 with the clutch in the clamp/fire position and the handle assembly actuated to move the drive rod of the handle assembly proximally.

The clutch 70 is slidably positioned about the tubular spacer 98 (FIG. 7) within the through bore 66 of the second bevel gear 64 and is movable between the articulation position (FIG. 8) and the clamp/fire position (FIG. 15). In the articulation position, the clutch 70 is engaged with the first articulation gear 100 and in the clamp/fire position, the clutch 70 is engaged with the screw nut 82.

Figure 11:
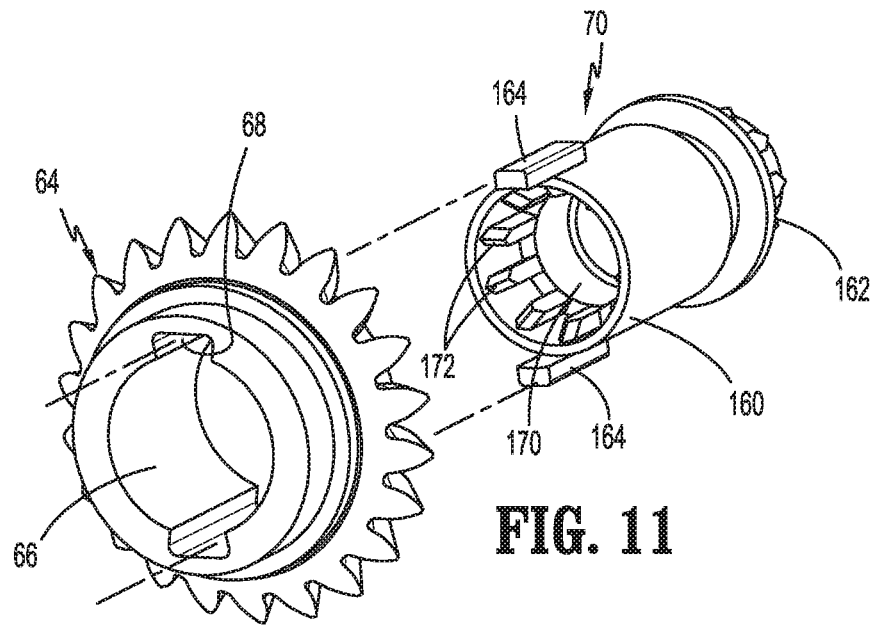
FIG. 11 is a side perspective view of a bevel gear and clutch of the handle assembly shown in FIG. 10 with the parts separated.
Figure 12:
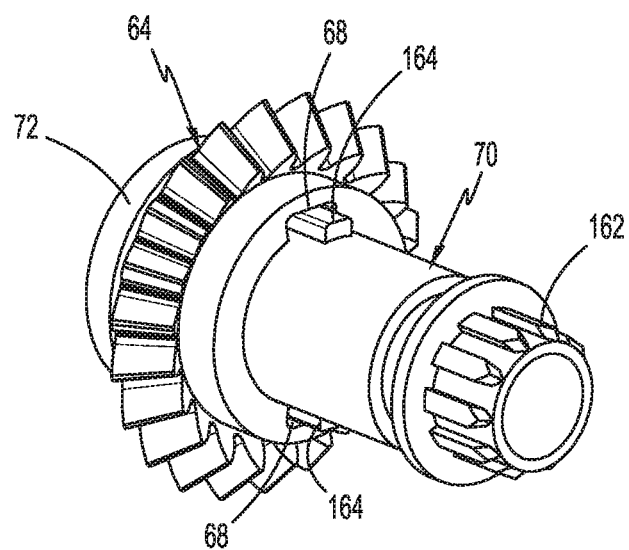
FIG. 12 is a side perspective view of the bevel gear and clutch shown in FIG. 11 with the parts assembled.

FIGS. 11 and 12 illustrate the clutch 70 and the second bevel gear 64. The clutch 70 includes a proximal portion 160 and a distal portion 162. The proximal portion 160 of the clutch 70 includes raised extensions 164 that extend in a proximal direction towards the screw nut 82 and are received within the longitudinal slots 68 in the second bevel gear 64. Receipt of the raised extensions 164 within the longitudinal slots 68 of the second bevel gear 64 rotatably couples the second bevel gear 64 to the clutch 70. Thus, when the motor 54 (FIG. 5) is energized to rotate the first bevel gear 58 and the second bevel gear 64 as described above, the clutch 70 rotates with the second bevel gear 64.

The clutch 70 defines a through bore 170 and includes internal splines 172. When the clutch 70 is in its clamp/fire position (FIG. 15), the splines 172 on the inner surface of the clutch 70 are engaged with the splines 96 on the screw nut 82. As such, when the motor 54 (FIG. 5) is energized to rotate the clutch 70, the screw nut 82 is also rotated. The distal portion 162 of the clutch 70 includes an annular flange 180 and defines an annular channel 182.

Figure 13:
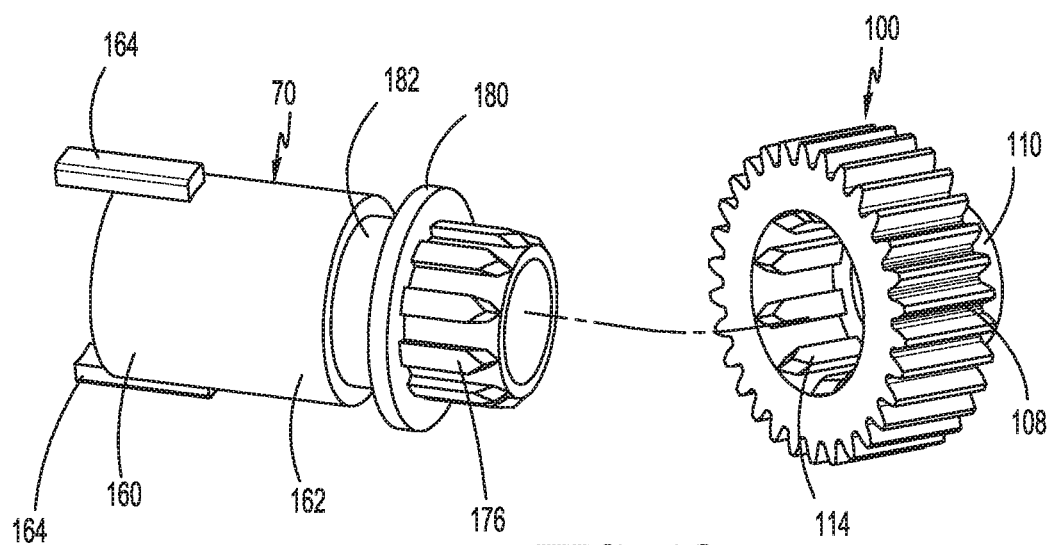
FIG. 13 is a side perspective view of an articulation gear and the clutch of the handle assembly shown in FIG. 10 with the parts separated.

FIG. 13 illustrates the clutch 70 and the first articulation gear 100. The distal portion of the clutch 70 supports a plurality of splines 176. When the clutch 70 is in the articulation position (FIG. 8), the splines 176 on the clutch 70 are engaged with the splines 114 of the first articulation gear 100 such that rotation of the clutch 70 causes rotation of the first articulation gear 100.

FIG. 6 illustrates a selector switch assembly 190 of the handle assembly 12 that is provided to allow a clinician to move the clutch 70 between the articulation and clamp/fire positions. The selector switch assembly 190 includes the clutch switch 22 and a fork 192. The clutch switch 22 includes a finger engagement member 196 and a base portion 198 that extends from the finger engagement member 196 into the housing 40 of the handle assembly 12. The fork 192 is secured to the clutch switch 22 by a pin 200 that extends through the base portion 198 of the clutch switch 22 and is received in an opening 202 formed in the fork 192. The fork 192 includes spaced tines 206 that are received within the annular channel 182 of the clutch 70. When the clutch switch 22 is moved longitudinally along the housing 40 of the handle assembly 12, the clutch 70 is moved longitudinally within the housing 40 along the tubular spacer 98 between the articulation position and the clamp/fire position.

FIGS. 5 and 8 illustrate a manual retraction mechanism 210 of the handle assembly 12 of the surgical stapling device 10 (FIG. 1). The manual retraction mechanism 210 includes tubular body portion 212 and a proximal handle portion 214. The tubular body portion 214 is received about the drive screw 80. The proximal handle portion projects from the proximal portion of the housing 40 of the handle assembly 12 and is rotatably secured to the drive screw 80 by a pin 216 such that rotation of the handle portion 214 of the manual retraction mechanism 210 causes rotation of the drive screw 80 in relation to the screw nut 82 to advance the drive screw 80 within the handle assembly 12. The handle assembly 12 may include a proximal cover 220 to enclose the proximal handle portion 214 of the manual retraction mechanism 210 when not needed. The manual retraction mechanism 210 can be used in the event of failure of the electrical components of the stapling device 10 (FIG. 1) to actuate the tool assembly 216 (FIG. 1), e.g., return the tool assembly 16 to a retracted or unactuated position.

FIG. 5 illustrates a safety switch assembly 230 that is coupled to the PCB 62. The safety switch assembly 230 is provided to prevent inadvertent firing of the stapling device 10 and must be pressed to activate the stapling device 10 (FIG. 1) before the stapling device 10 can be fired. The safety switch assembly 230 will not be described in detail herein.

Figure 9:
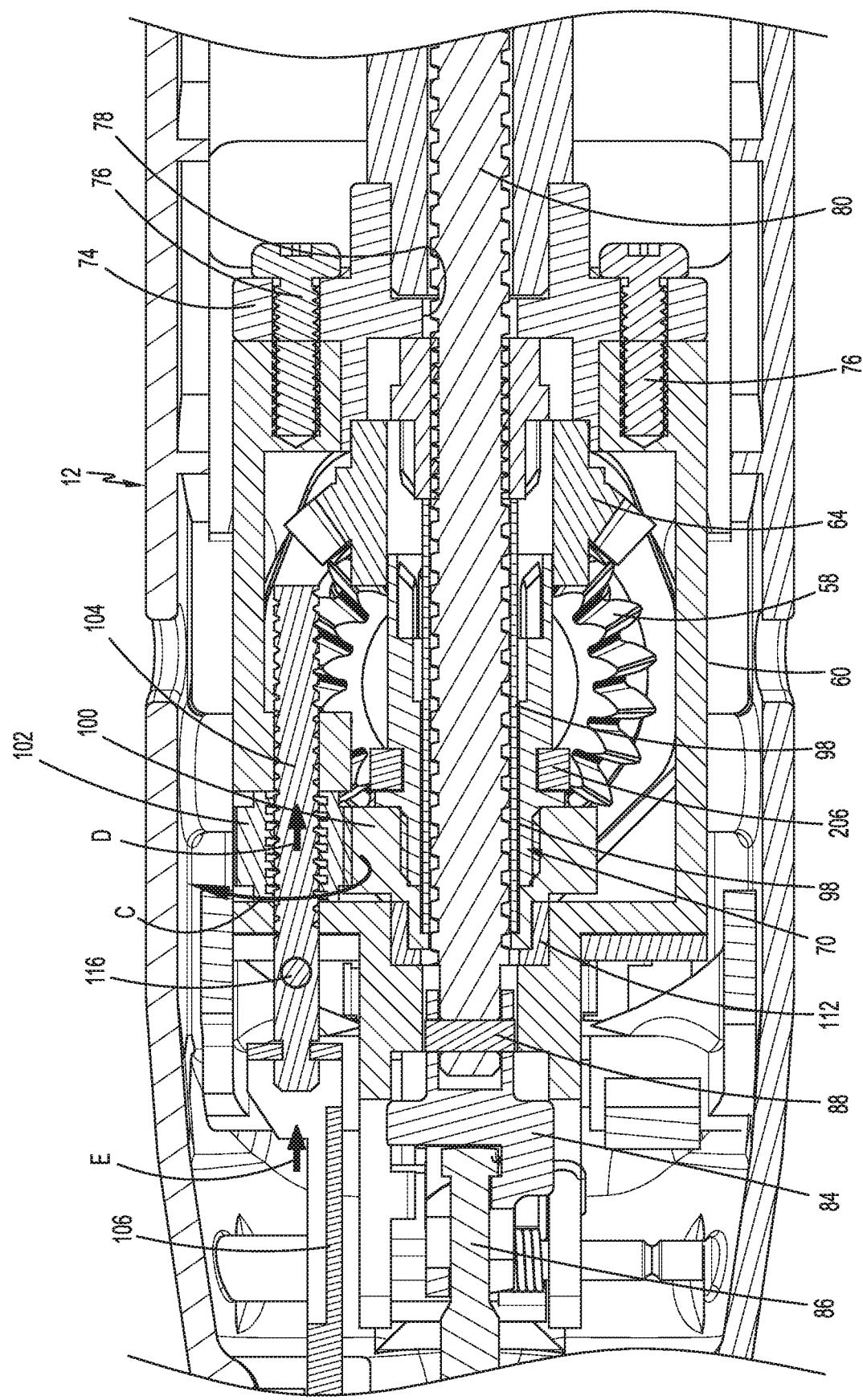
FIG. 9 is a cross-sectional view of the handle assembly with the clutch in the articulation position as the articulation mechanism is actuated.
Figure 10:
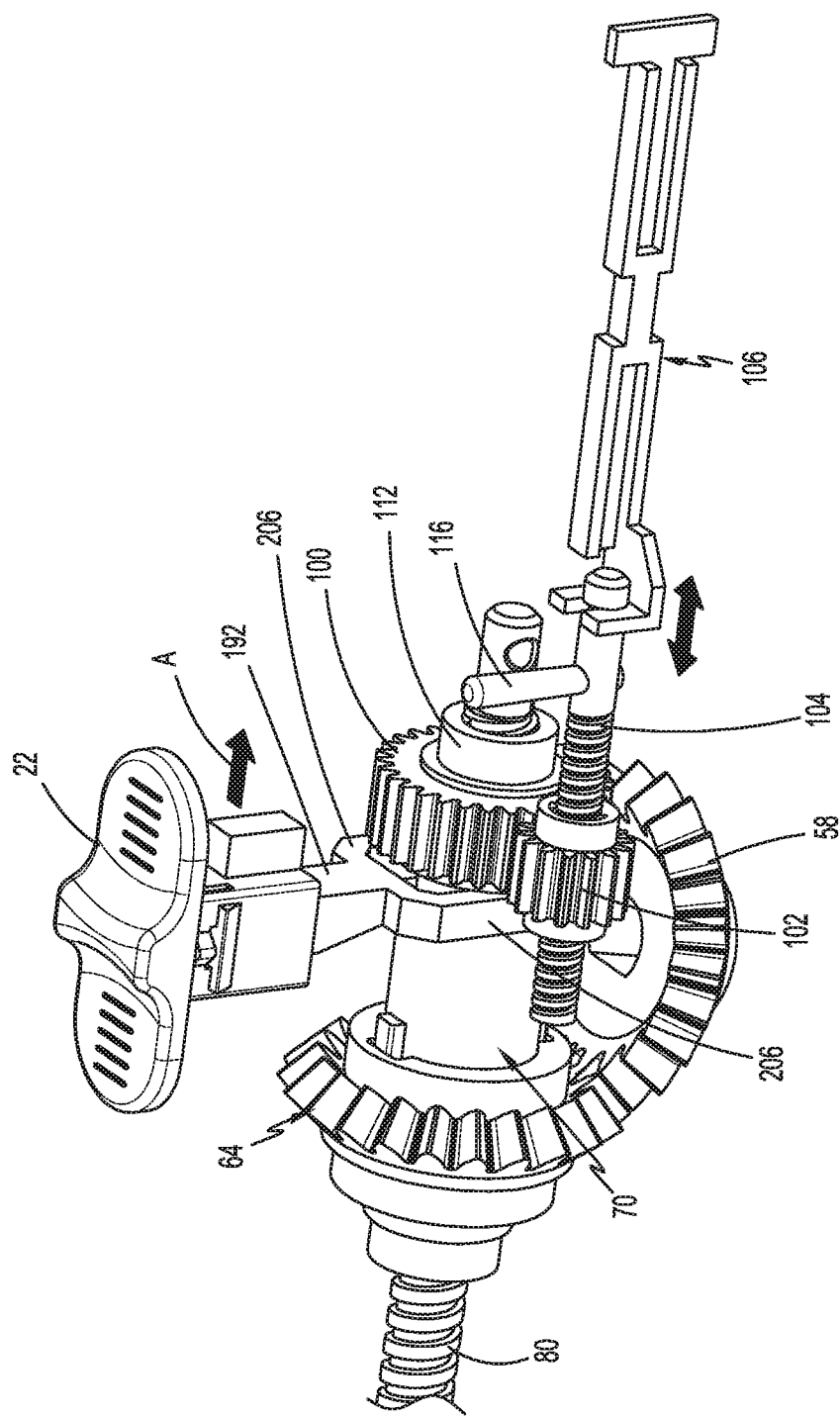
FIG. 10 is a side perspective view of the articulation mechanism and clutch of the handle assembly of the surgical device shown in FIG. 1 with the clutch in the articulation position.
Figure 14:
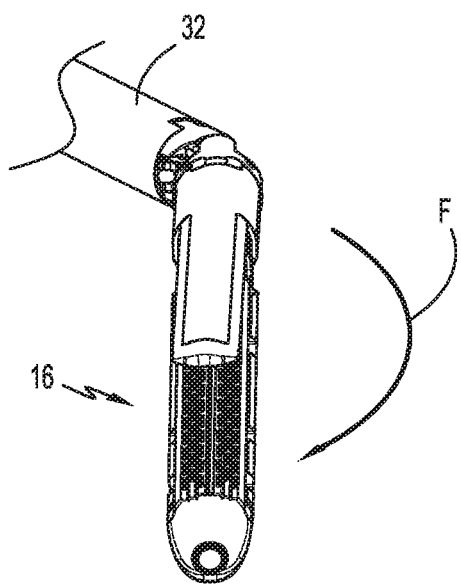
FIG. 14 is a side perspective view of the tool assembly of the surgical stapling device shown in FIG. 1 with the tool assembly in an articulated position.

FIGS. 8-10 illustrate the stapling device 10 as the clutch switch 22 is moved to the articulation position. When the clutch switch 22 is slid in a distal direction as indicated by arrow "A" in FIG. 8, the clutch 70 is moved about the tubular spacer 98 in the direction of arrow "B" to move the splines 176 (FIG. 13) on the distal portion 162 of the clutch 70 into engagement with the splines 114 on the first articulation gear 100. As illustrated, the engaging ends of the splines 114 and 176 can be tapered to allow the splines to self-align. When the motor 54 is energized, the motor 54 rotates the first bevel gear 58 which is engaged with and rotates the second bevel gear 64. As described above, the second bevel gear 64 is engaged with the clutch 70 such that rotation of the second bevel gear 64 rotates the clutch 70. In the articulation position, the clutch 70 is engaged with the first articulation gear 100. Rotation of the first articulation gear 100 causes rotation of the second articulation gear 102 about the articulation screw 102 in the direction indicated by arrow "C" in FIG. 9 to move the articulation screw 104 longitudinally in the direction of arrow "D". The articulation screw 104 is coupled to the articulation link 106 such that longitudinal movement of the articulation screw 104 causes longitudinal movement of the articulation link 106 in the direction of arrow "E" in FIG. 9. As described above, longitudinal movement of the articulation link 106 causes longitudinal movement of the articulation body 130, the articulation plate 132, and the articulation rod 134 to articulate the tool assembly 16 in the direction of arrow "F" in FIG. 14.

FIGS. 15-20 illustrate the clutch 70 in the clamp/fire position. When the clutch switch 22 is moved proximally along the outer surface of the housing 40 in the direction of arrow "G" in FIG. 15, the clutch 70 is moved proximally along the tubular spacer 98 in the direction of arrows "H" in FIG. 15 to move the splines 172 (FIG. 18) of the clutch 70 into engagement with the splines 96 (FIG. 18) of the screw nut 82. When this occurs, the clutch 70 will disengage from the first articulation gear 100. In the clamp/fire position, when the motor 54 is energized, the motor 54 rotates the first bevel gear 58 which is engaged with and rotates the second bevel gear 64. As described above, the second bevel gear 64 is engaged with the clutch 70 such that rotation of the second bevel gear 64 rotates the clutch 70 in the direction of arrow "I" in FIG. 19. As the clutch 70 is rotated, the screw nut 82 also rotates about the drive screw 80 to move the drive screw 80 longitudinally in the direction of arrow "J". As described above, the drive screw 80 is coupled to the drive rod 86 and moves the drive rod 86 longitudinally within the adapter assembly 14 (FIG. 1).

The PCB 62 (FIG. 5) is electrically coupled to battery pack 44, the motor 54, the actuation button 20, and the safety switch assembly 230. The PCB 62 accommodates a motor controller, switches that are coupled to the actuation button 20 (FIG. 3), and a processor or controller that controls operation of the handle assembly 10 to control actuation of the tool assembly 16 (FIG. 1). The controller can include any suitable electrical components for operating the disclosed surgical device or components thereof. The controller may include any type of computing device, computational circuit, or any type of processor or processing circuit capable of executing a series of instructions that are stored in memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include a memory to store data and/or instructions that, when executed by the one or more processors, cause the one or more processors to perform one or more methods and/or algorithms.

Figure 20:
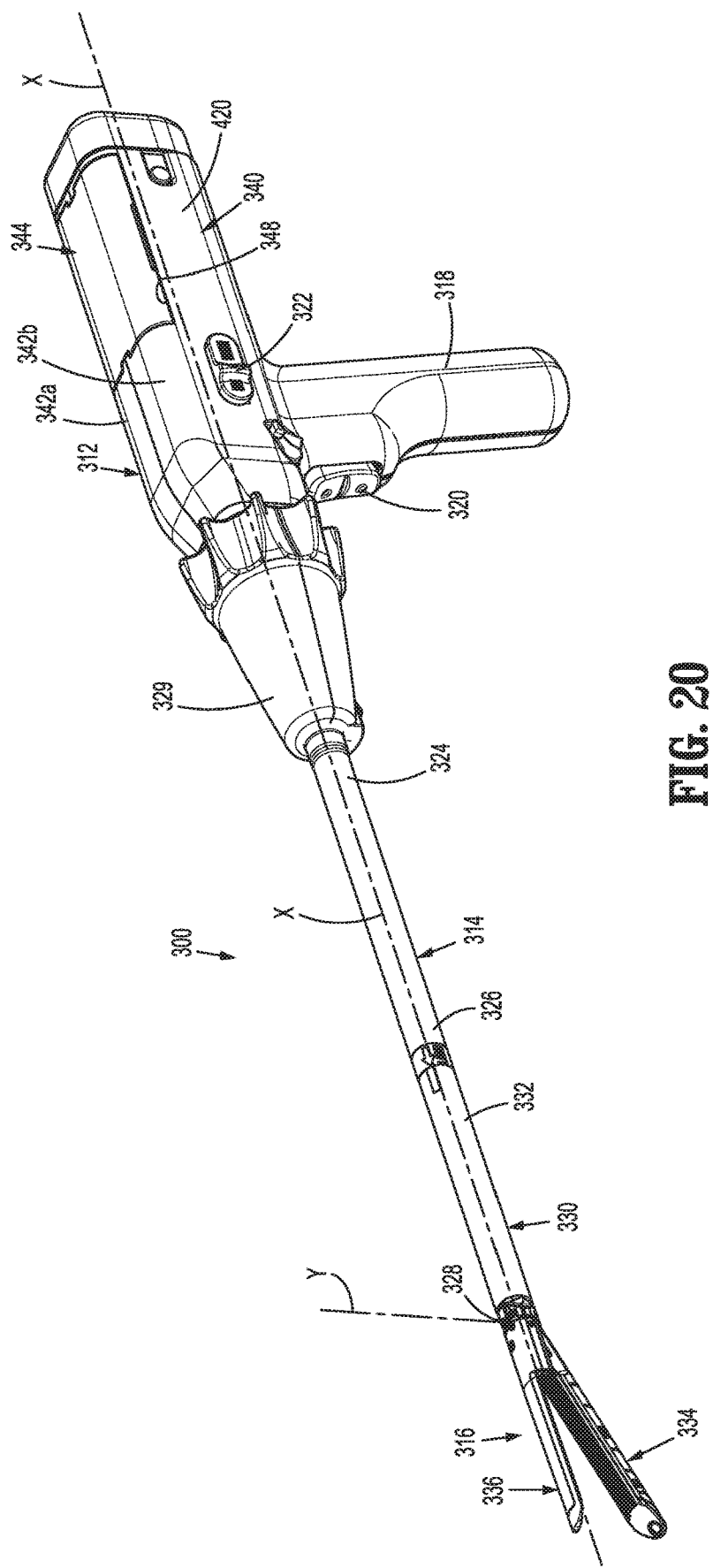
FIG. 20 is a side perspective view from a distal end of an alternate version of the disclosed powered surgical device with a tool assembly in a non-articulated position.

FIGS. 20-32 illustrate an alternate version of the stapling device 10 (FIG. 1) shown generally as stapling device 300. FIG. 20 illustrates the stapling device 300 which includes a handle assembly 312, an elongate body or adapter assembly 314, and a tool assembly 316. The handle assembly 312 includes a stationary handle portion 318, an actuation button 320, and clutch switches 322. One clutch switch is positioned on each side of the handle assembly 312. The adapter assembly 314 defines a longitudinal axis "X" and includes a proximal portion 324 that is coupled to the handle assembly 312, and a distal portion 326 that supports the tool assembly 316. The tool assembly 316 is secured to the distal portion 326 of the adapter assembly 314 by a pivot member 328 that defines an axis "Y" that is transverse to the longitudinal axis "X". The tool assembly 16 can articulate about the axis "Y" between an articulated position in which the tool assembly 16 is aligned with the longitudinal axis "Y" and non-articulated positions in which a longitudinal axis of the tool assembly and the longitudinal axis "X" define acute angles. The proximal portion 324 of the adapter assembly 314 is supported within a rotation knob 329 that is rotatably coupled to a distal portion of the handle assembly 312. The rotation knob 329 is manually rotatable about the longitudinal axis "X" to rotate the adapter assembly 314 and the tool assembly 316 about the longitudinal axis "X" in relation to the handle assembly 312.

In aspects of the disclosure, the tool assembly 316 forms part of a reload assembly 330 that includes a proximal body portion 332 having a proximal end and a distal end. The proximal end of the proximal body portion 332 is releasably coupled to the distal portion 326 of the adapter assembly 14 and the distal end of the proximal body portion 332 supports the tool assembly 316. The reload assembly 330 can be removed from the adapter assembly 314 and replaced to facilitate reuse of the adapter assembly 314 and handle assembly 12 during a surgical procedure. Alternately, the tool assembly 316 can be secured directly to the distal portion 326 of the adapter assembly 314.

I aspects of the disclosure, the tool assembly 316 is a stapling device and includes a cartridge assembly 334 and an anvil 336 that are movable in relation to each other between open and clamped positions. In aspects of the disclosure, the anvil 336 is fixedly secured to the proximal body portion 332 of the reload assembly 330 and the cartridge assembly 334 pivots in relation to the anvil assembly 326 and proximal body portion 332 between the open and clamped positions. It is envisioned that the cartridge assembly 334 can be fixedly mounted to the proximal body portion 332 of the reload assembly 330 and the anvil 336 can pivot between the open and clamped positions. Although the tool assembly 316 is illustrated in the form of a stapling device, it is envisioned that the tool assembly 316 may include a variety of different types of surgical devices including graspers, vessel sealers, clip appliers, stitching devices or the like.

FIGS. 21-24 illustrate the handle assembly 312 of the stapling device 310 which includes a body 340 (FIG. 20) formed of first and second half-sections 342a and 342b and a battery pack 344. The first and second half-sections 342a and 342b are coupled together to form the stationary handle portion 318 (FIG. 20) and define a cavity 346 (FIG. 22) and a recess 348 (FIG. 20) that receives the battery pack 344. The battery pack 344 is substantially similar to the battery pack 44 (FIG. 5) and will not be described in further detail herein.

The stationary handle portion 318 of the body 340 of the handle assembly 212 defines a portion of the cavity 346 (FIG. 22) and receives a motor 354 (FIG. 21) that has a motor shaft (not shown). The motor shaft is secured to a first bevel gear 358 (FIG. 23) such that operation of the motor 354 causes rotation of the first bevel gear 358. The handle assembly 312 includes a gear housing 360 (FIG. 21) that is secured above the stationary handle portion 318 of the body 340 of the handle assembly 312 to the body 340 with, e.g., screws 361 (FIG. 23) such that the first bevel gear 358 is positioned within the gear housing 360. The gear housing 360 has a top surface as viewed in FIG. 21 that supports a printed circuit board 362 ("PCB") which is electrically coupled to the actuation button 320 and to the battery pack 344.

The handle assembly 312 includes a second bevel gear 364 (FIG. 23) that is engaged with the first bevel gear 358 and is positioned within the gear housing 360. The second bevel gear 364 defines a central through bore 366 (FIG. 24) and longitudinal slots 368 (FIG. 24) that extend along a length of the central through bore 366. The longitudinal slots 368 are provided to couple the second bevel gear 364 to a clutch 370 described in further detail below. The second bevel gear 364 is coupled to the first bevel gear 358 such that rotation of the first bevel gear 358 about a first axis causes rotation of the second bevel gear 364 about a second axis that is substantially perpendicular to the first axis.

The handle assembly 312 includes a support member 374 (FIG. 23) that is secured to the gear housing 360 and includes a stepped cylindrical body 375 that defines a through bore 378. The stepped cylindrical body 375 (FIG. 22) has a distal portion 375a and a proximal portion 375b. The distal portion 375a of the support member 374 extends through an opening in the gear housing 360 into the gear housing 360. The second bevel gear 364 (FIG. 24) includes a proximal hub portion 372 (FIG. 24) that is supported for rotation within the distal portion 375a (FIG. 23) of the support member 374. In aspects of the disclosure, the support member 374 is fixedly secured to the gear housing 360 within the body 340 of the handle assembly 312 by screws or the like.

Figure 24:
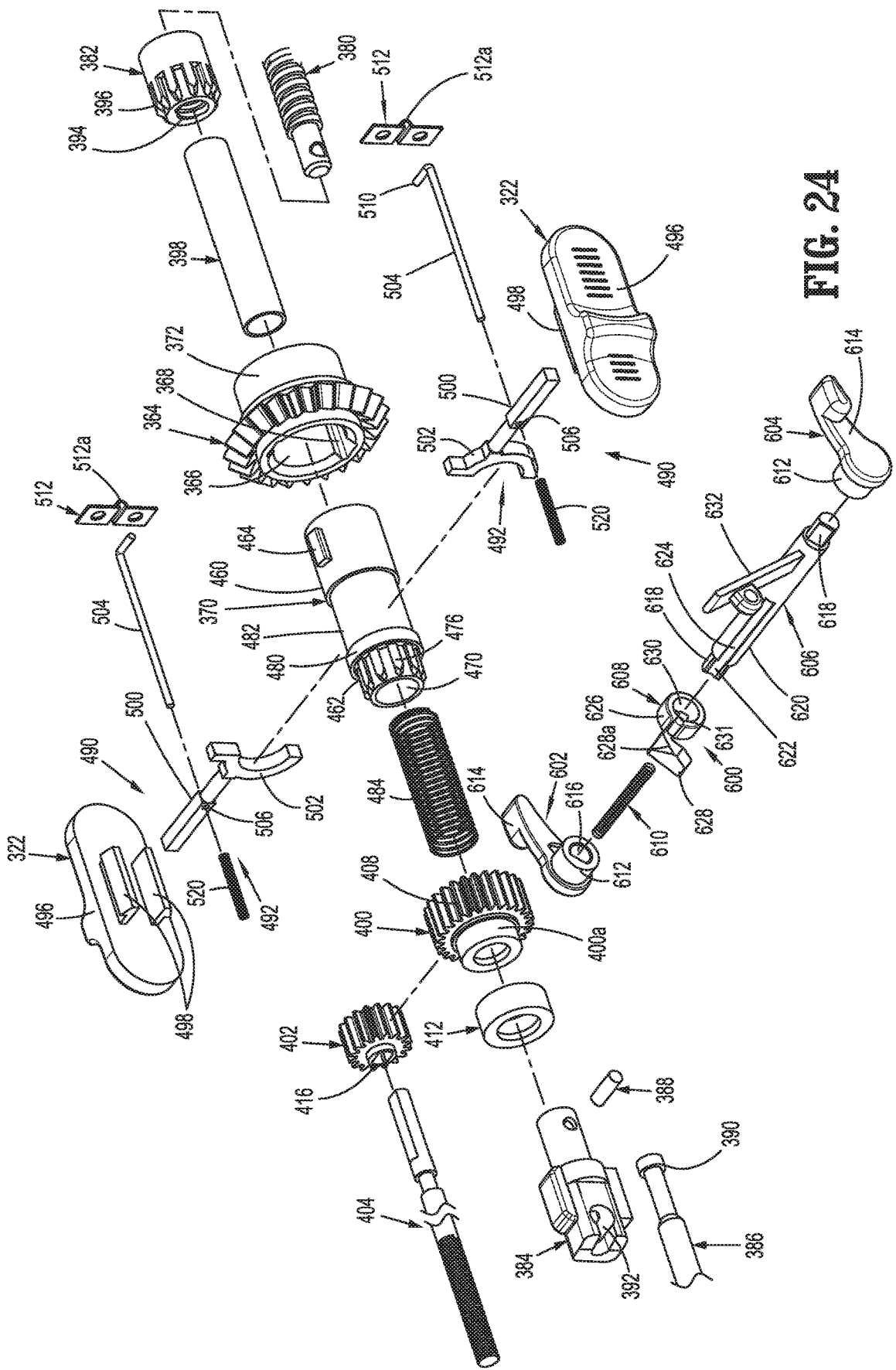
FIG. 24 is an exploded perspective view of the drive assembly, articulation mechanism, selector switch assembly, and safety toggle mechanism of the handle assembly shown in FIG. 23.
Figure 25:
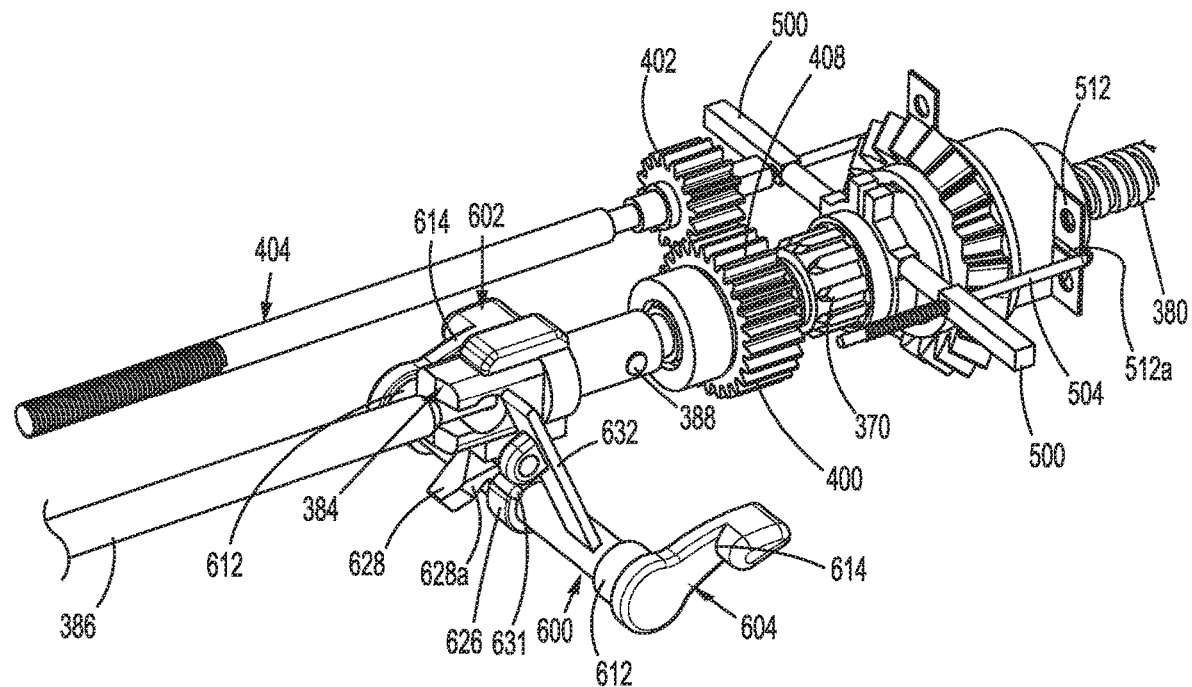
FIG. 25 is a side perspective view from one side of the drive assembly, the articulation mechanism, the safety toggle mechanism, and selector switch assembly of the handle assembly shown in FIG. 24 with the components assembled and clutch switches of the selector switch assembly removed.
Figure 26:
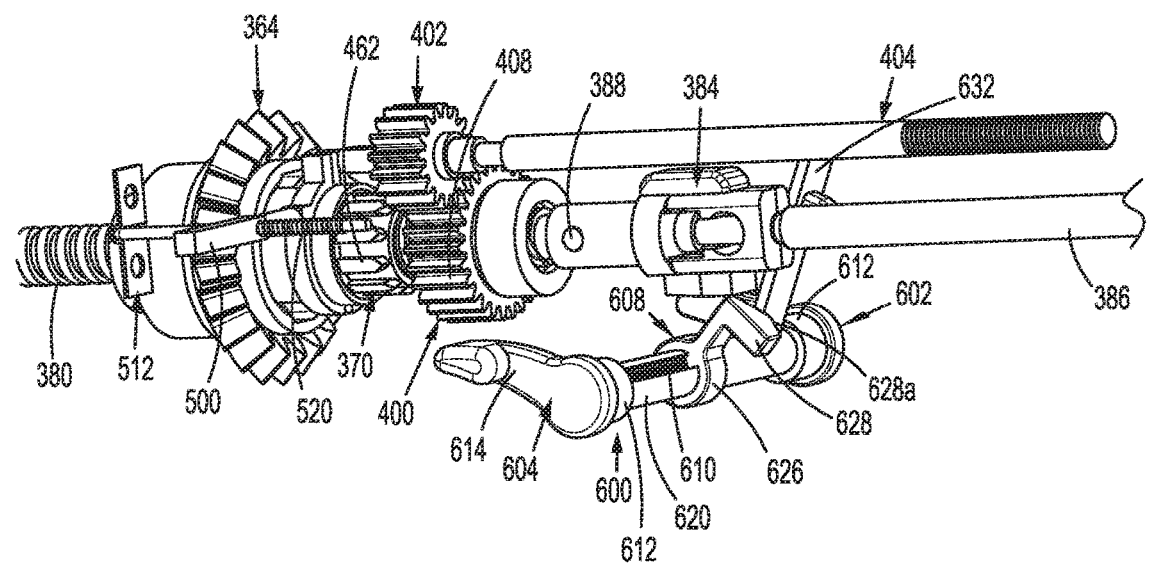
FIG. 26 is a side perspective view from the other side of the drive assembly, the articulation mechanism, the safety toggle mechanism, and selector switch assembly of the handle assembly shown in FIG. 24 with the components assembled and clutch switches of the selector switch assembly removed.
Figure 27:
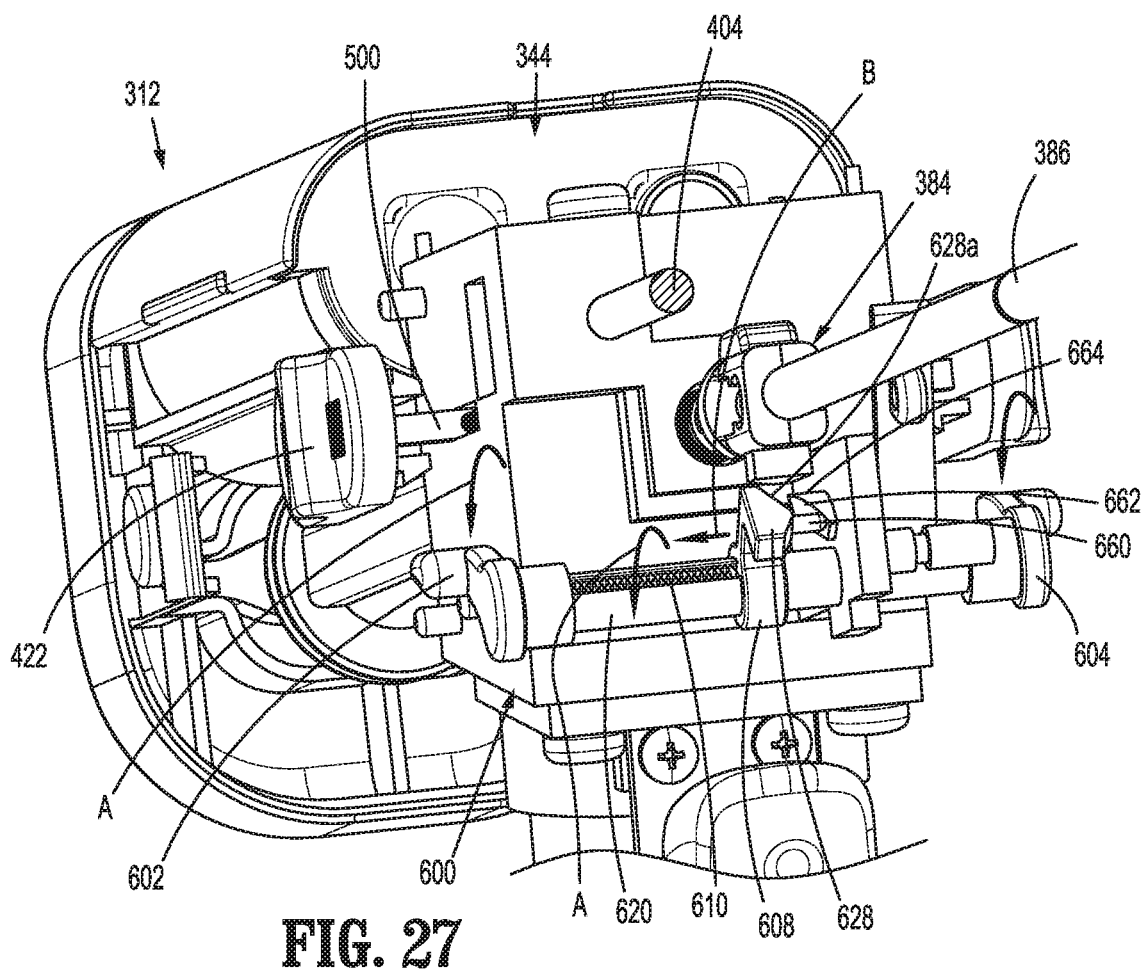
FIG. 27 is a perspective view from a distal end of the handle assembly shown in FIG. 21 with the body half-sections and an articulation linkage of an articulation mechanism of the handle assembly removed as the safety toggle mechanism moves towards an activated position.

FIGS. 24-26 illustrate components of a drive assembly of the handle assembly 312 (FIG. 20). The drive assembly includes a drive screw 380, a screw nut 382 (FIG. 24), a coupling member 384, and a drive rod 386. The drive screw 380 extends through the through bore 378 of the support member 374 (FIG. 22) and has a proximal portion and a distal portion. The distal portion of the drive screw 380 is fixedly coupled to a proximal portion of the coupling member 384 by a pin 388 (FIG. 25). The coupling member 384 includes a distal portion that is coupled to a proximal portion of the drive rod 386. In aspects of the disclosure, the proximal portion of the drive rod 386 includes a stepped portion 390 that is received within a slot 392 (FIG. 6) in the distal portion of the coupling member 384 to axially fix the drive rod 386 to the coupling member 384 but allow the drive rod 386 to rotate in relation to the coupling member 384. The components on the drive assembly are coupled such that the longitudinal movement of the drive screw 380 causes longitudinal movement of the drive rod 386.

The screw nut 382 is received partly within the central through bore 366 (FIG. 24) of the second bevel gear 364 and within the distal portion 375a (FIG. 23) of the support member 364. The screw nut 382 defines a threaded through bore 394 and includes external gear teeth or splines 396 (FIG. 24). The threaded through bore 394 receives the drive screw 380 to threadedly couple the screw nut 382 about the drive screw 380. The splines 396 engage the clutch 370 when the clutch 370 is in a clamp/fire position as described in further detail below.

A tubular spacer 398 is received about the drive screw 380 and engages a distal portion of the screw nut 382 to maintain the axial position of the screw nut 382 within the body 340 (FIG. 1) of the handle assembly 312. The tubular spacer 398 also supports the clutch 370 for longitudinal movement between the clamp/fire position and an articulation position as described in further detail below.

Figure 21:
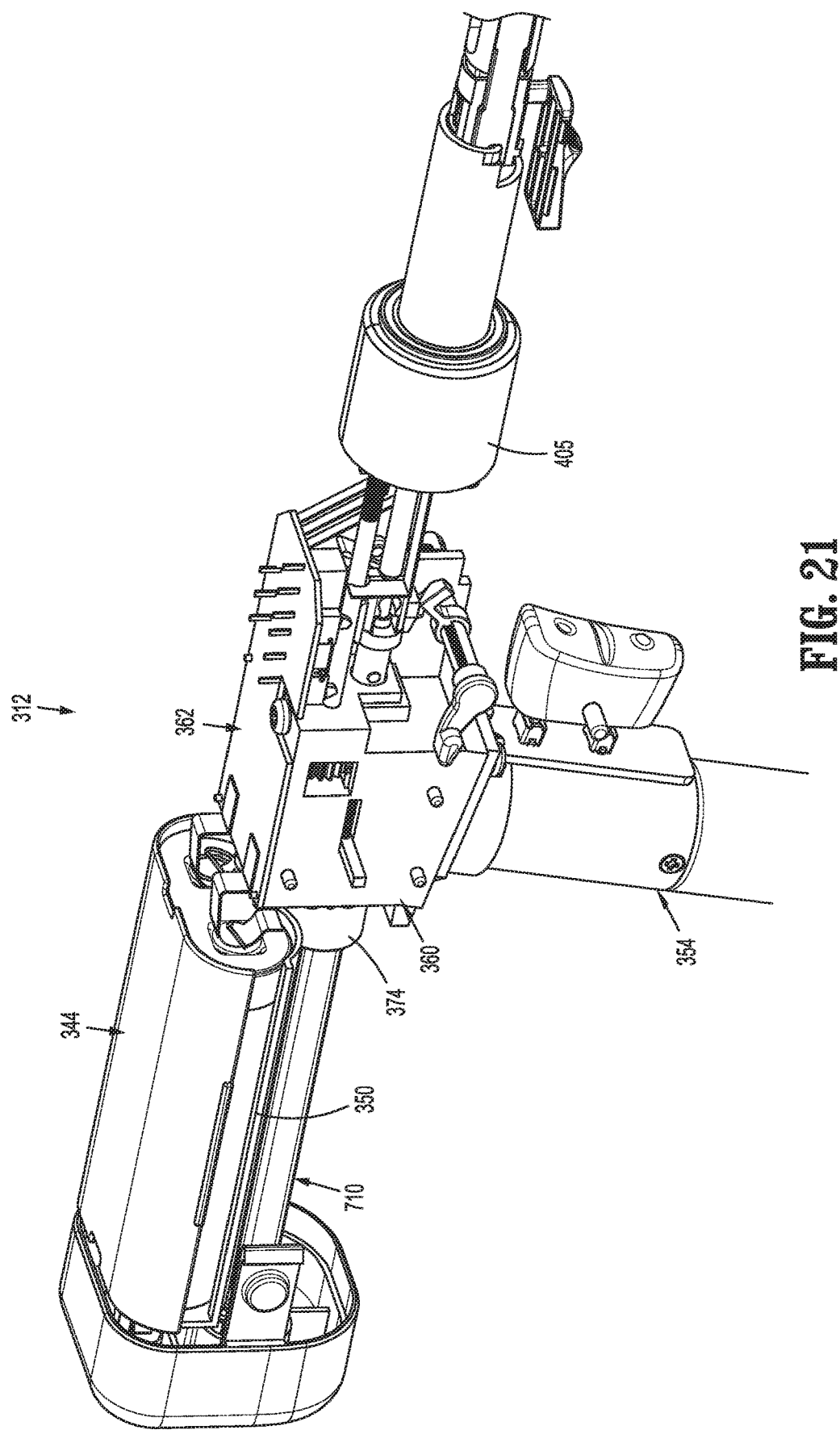
FIG. 21 is a side perspective view of the handle assembly of the surgical device shown in FIG. 1 with housing half-sections removed.
Figure 22:
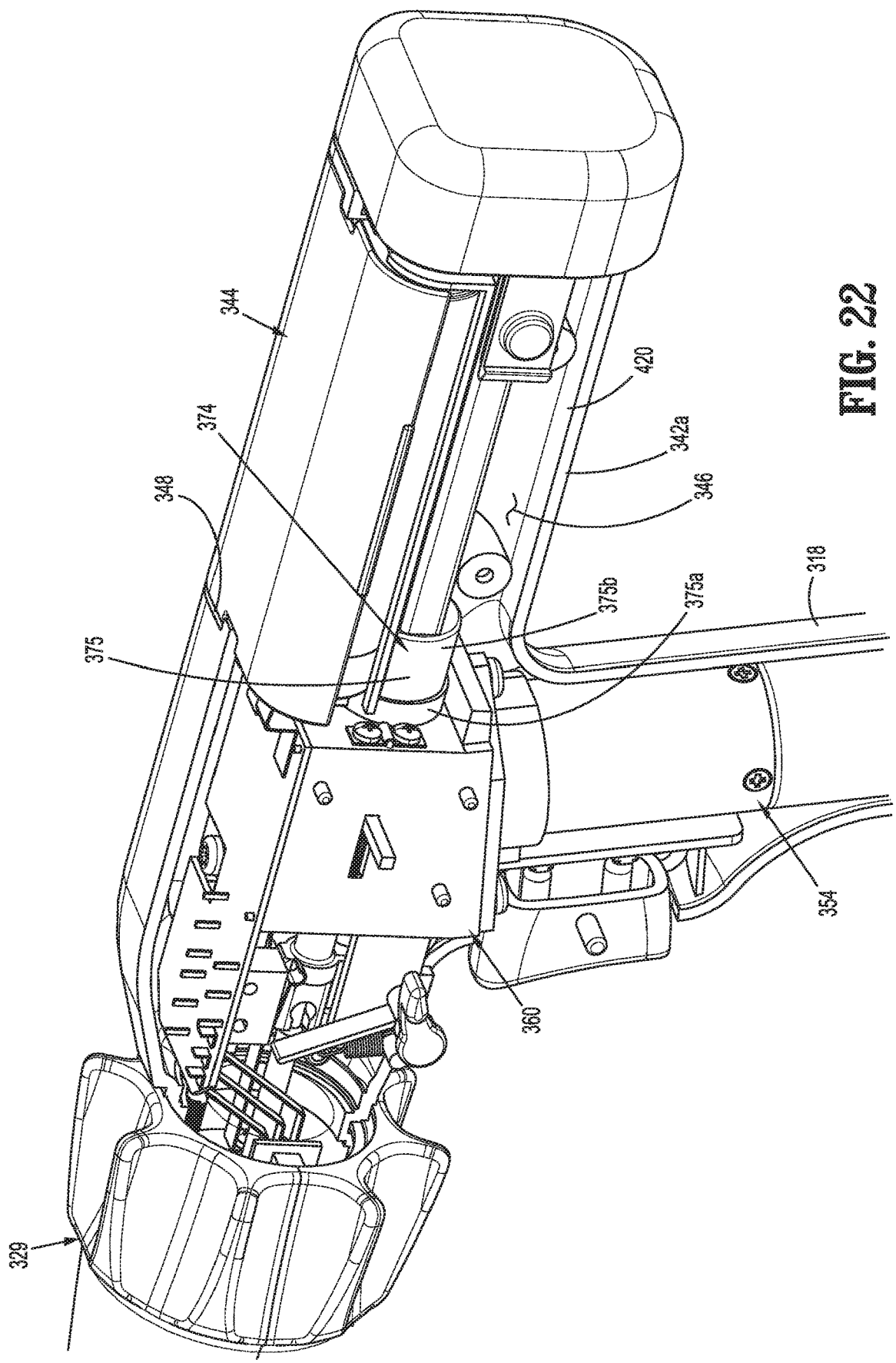
FIG. 22 is a side perspective view of the handle assembly shown in FIG. 21 with one of the housing half-sections removed.
Figure 23:
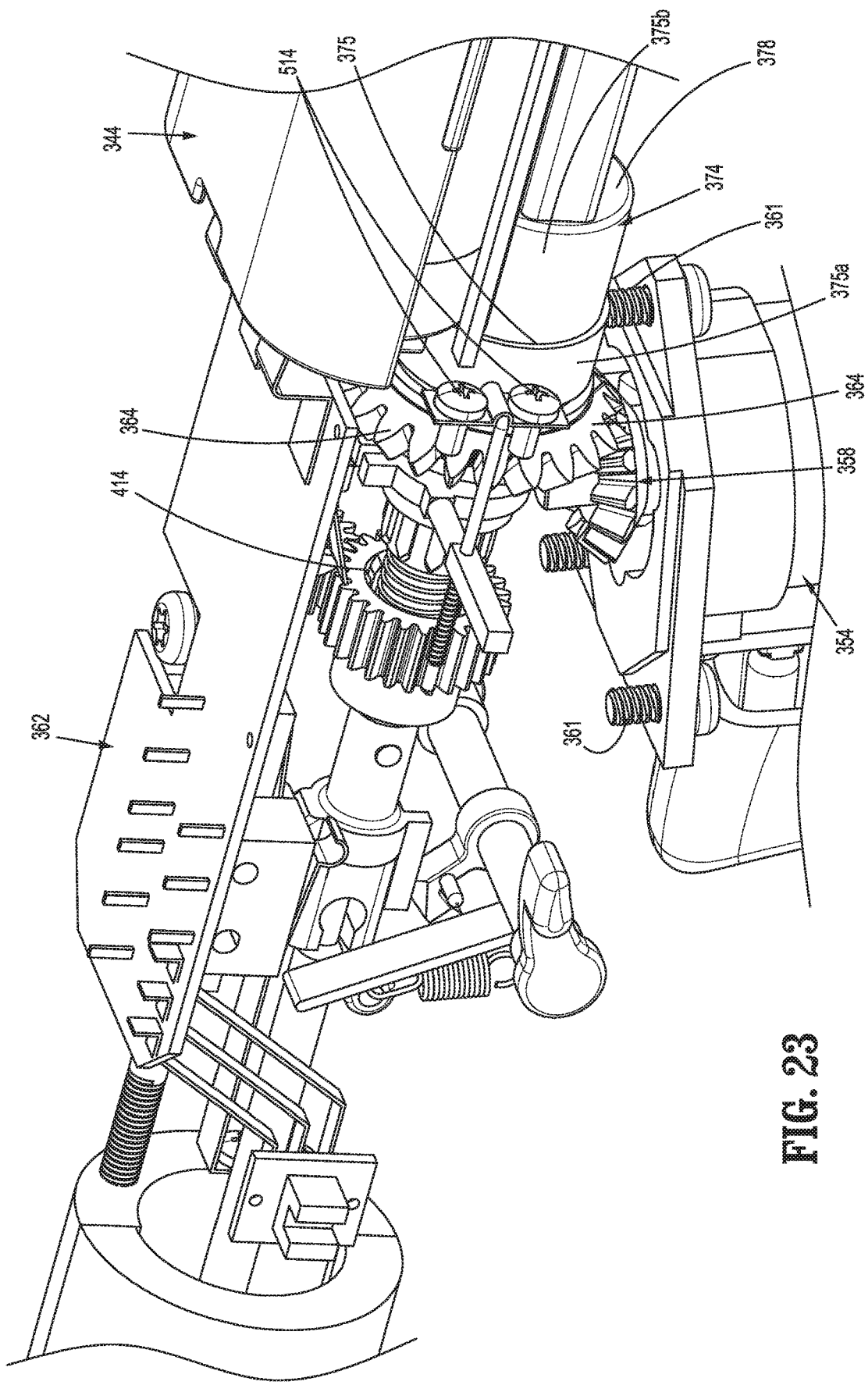
FIG. 23 is a side perspective view of the handle assembly shown in FIG. 22 with the housing half-sections and a gear housing.

The handle assembly 312 (FIG. 20) includes an articulation mechanism that includes a first articulation gear 400, a second articulation gear 402, an articulation screw 404, and an articulation link (not shown). The first articulation gear 400 is supported for rotation on the gear housing 360 and includes outer gear teeth 408. In aspects of the disclosure, the first articulation gear 400 includes a distally extending hub 400a (FIG. 24) that is rotatably supported on a bearing 412 (FIG. 24) supported on the gear housing 360 (FIG. 21). The first articulation gear 400 and the bearing 412 define central openings that facilitate passage of the drive screw 380 to a position distally of the first articulation gear 400 and the bearing 412. The central opening of the first articulation gear 400 is defined by an annular array of splines 414 (FIG. 23) that are engaged by the clutch 370 when the clutch 370 is moved to the articulation position.

The second articulation gear 402 is rotatably supported on the gear housing 360 and is engaged with the first articulation gear 400. The second articulation gear 402 defines a non-circular through bore 416 that receives a non-circular end of the articulation screw 404 to rotatably fix the second articulation gear 402 to the articulation screw 404. The second articulation gear 402 is axially fixed to the gear housing 360 within the body 340 of the handle assembly 312 (FIG. 1) such rotation of the second articulation gear 402 causes rotational movement of the articulation screw 404. The articulation screw 404 includes a distal portion that is coupled to a proximal portion of the articulation link (not shown) by a coupling 405 (FIG. 21) such that rotational movement of the articulation screw 404 causes longitudinal movement of the articulation link within the elongate body 314 (FIG. 20) of the stapling device 310.

Although not described in detail herein, the stapling device 300 includes an articulation assembly similar to the articulation assembly 124 shown in FIG. 5 and described in detail above which connects the articulation screw 404 to the tool assembly 316 (FIG. 20). The articulation mechanism of the handle assembly 312 (FIG. 1) operates in a manner similar to the articulation mechanism of the handle assembly 12 (FIG. 1) and will not be described in further detail herein.

The clutch 370 is slidably positioned about the tubular spacer 398 (FIG. 24) within the through bore 366 of the second bevel gear 364 and is movable between an articulation position and a clamp/fire position. In the articulation position, the clutch 370 is engaged with the first articulation gear 400 such that rotation of the clutch 370 effects rotation of the first articulation gear 400 to move the tool assembly 316 (FIG. 20) between non-articulated and articulated positions as described above regarding the stapling device 10. In the clamp/fire position, the clutch 370 is engaged with the screw nut 382 such that rotation of the clutch 370 causes rotation of the screw nut 382 moves the drive assembly including the drive rod 386 longitudinally within the stapling device 300 to actuate the tool assembly 316 (FIG. 20) as described above regarding the stapling device 10.

FIG. 24 illustrates the clutch 370 and the second bevel gear 364. The clutch 370 includes a proximal portion 460 and a distal portion 462. The proximal portion 460 of the clutch 370 includes raised extensions 464 that extend in a longitudinally towards the screw nut 382 and are received within the longitudinal slots 368 in the second bevel gear 364. Receipt of the raised extensions 464 within the longitudinal slots 368 of the second bevel gear 364 rotatably couples the second bevel gear 364 to the clutch 370. Thus, when the motor 354 (FIG. 22) is energized to rotate the first bevel gear 358 and the second bevel gear 364 as described above, the clutch 370 rotates with the second bevel gear 364.

The clutch 370 defines a through bore 470 and includes internal splines (not shown) like splines 172 (FIG. 11) of the clutch 70. When the clutch 370 is in its clamp/fire position, the splines on the inner surface of the clutch 370 are engaged with the splines 396 on the screw nut 382. As such, when the motor 54 (FIG. 22) is energized to rotate the clutch 370, the screw nut 382 is also rotated. The distal portion 462 of the clutch 370 includes an annular flange 480 and defines an annular channel 482.

The clutch 370 and the first articulation gear 400 are rotatably coupled to each other when the clutch 370 is in the articulation position. More specifically, the distal portion of the clutch 370 supports a plurality of splines 476. When the clutch 370 is in the articulation position (FIG. 8), the splines 476 on the clutch 470 are engaged with the splines 414 (FIG. 23) of the first articulation gear 400 such that rotation of the clutch 470 causes rotation of the first articulation gear 400.

The clutch 470 is biased towards the clamp/fire position by a biasing member 484. In aspects of the disclosure, the biasing member 484 includes a coil spring although other types of biasing members are envisioned. The biasing member 484 is compressed between a distal face of the clutch 370 and the first articulation gear 400 such that the clutch 370 is urged proximally towards the screw nut 382.

The handle assembly 312 includes a selector switch assembly 490 that is similar to the selector switch assembly 190 (FIG. 6) of the handle assembly 12 and provides a clinician a mechanism to move the clutch 370 from the clamp/fire position to the articulation position. The selector switch assembly 490 includes clutch switches 322 and fork members 492. The clutch switches 322 are slidably positioned on opposite sides of the body 340 of the handle assembly 312 (FIG. 20) and include a finger engagement member 496 and extensions 498 that extend from the finger engagement member 496 through longitudinal slots (not shown) in the body 340 of the handle assembly 312. The extensions 498 are resilient and are received through the elongated slots (not shown) in the body 340 of the housing 312 in a snap-fit manner to slidably secure the clutch switches 322 to the body 340 (FIG. 20) of the handle assembly 312. Each of the fork members 492 includes a transverse rod 500 and a semi-circular coupling member 502. Each one of the transverse rods 500 is secured to a respective one of the clutch switches 322. In aspects of the disclosure, each of the clutch switches 322 defines a bore (not shown) that receives an end of a respective one of the transverse rods 500 to secure the clutch switches 322 to the transverse rods 500. Alternately, it is envisioned that the transverse rods 500 can be secured to the clutch switches 322 in a variety of different manners or the transverse rods 500 and the clutch switches 322 can be integrally formed. Each of the semi-circular coupling members 502 of the fork members 492 is received within the annular channel 482 of the clutch 370. When the clutch switch 322 is moved longitudinally along the body 340 of the handle assembly 312, the clutch 370 is moved longitudinally within the body 340 along the tubular spacer 398 against the urging of the biasing member 484 from the clamp/fire position to the articulation position.

Figure 30:
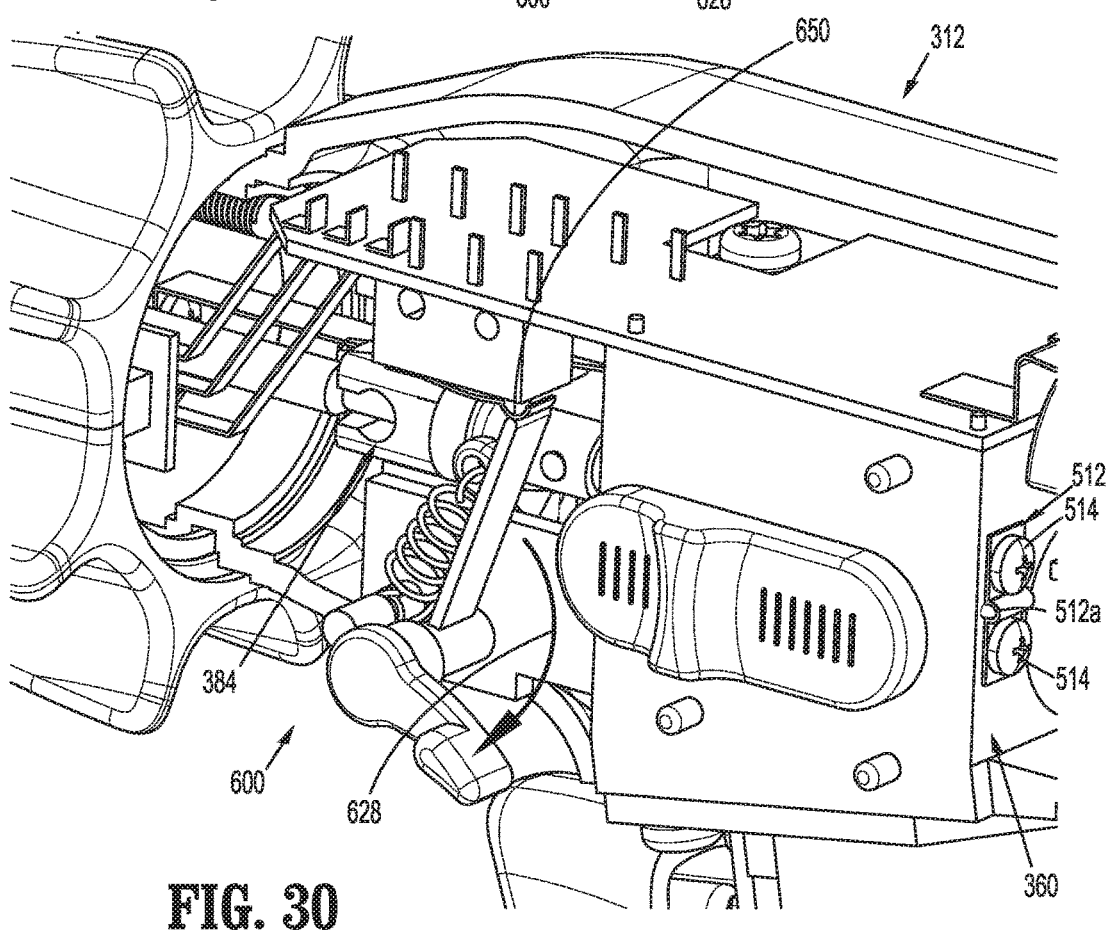
FIG. 30 is a perspective view of the handle assembly shown in FIG. 29 with one of the body half-sections and an articulation linkage of an articulation mechanism of the handle assembly removed with the safety toggle mechanism in the activated position.
Figure 31:
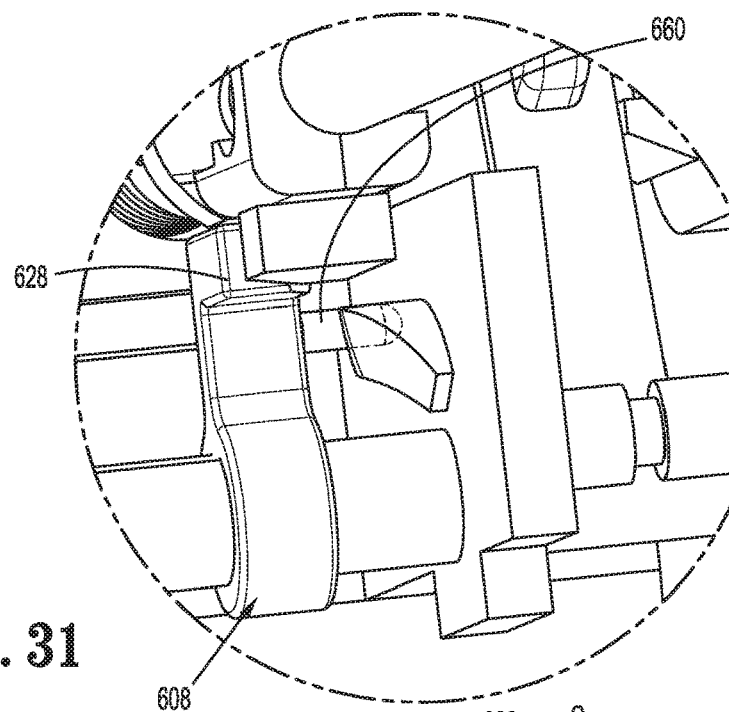
FIG. 31 is an enlarged view of the indicated area of detail shown in FIG. 29.

In aspects of the disclosure, the handle assembly 312 includes guide rods 504 that are supported within the body 340 of the handle assembly 312 and extend in a direction that is parallel to the longitudinal axis "X" (FIG. 20) of the elongate body 314. Each of the guide rods 504 is supported within the body 340 of the handle assembly 312 and extends through an opening 506 in a respective one of the transverse rods 500 of the selector switch assembly 490. The guide rods 504 guide movement of the fork members 492 of the selector switch assembly 490 as the selector switch assembly 490 is moved from a retracted position to an advanced position to move the clutch 370 from the clamp/fire position to the articulation position. In aspects of the disclosure, each of the guide rods 504 has an L-shaped configuration and includes a proximal transverse portion 510. The proximal transverse portion 510 is received within a slot 512a of a bracket 512 and the bracket 512 is secured to the gear housing 360 with screws 514 (FIG. 30).

In some aspects of the disclosure, the selector switch assembly 490 includes biasing members 520 that are positioned to urge the fork members 492 of the selector switch assembly 490 proximally to urge the clutch 370 towards the clamp/fire position. The biasing members 520 can be coil springs although other types of biasing members are envisioned.

FIGS. 24-26 illustrate a safety toggle mechanism 600 which includes first and second toggle members 602 and 604, a shaft 606, a safety slider 608, and a biasing member 610 (FIG. 24). Each of the safety toggles 602 and 604 includes a hub 612 and a lever 614. The hubs 612 are rotatably supported in openings (not shown) defined in opposite sides of the body 340 of the handle assembly 312 (FIG. 20) and define D-shaped bores 616 (FIG. 24). The shaft 606 has first and second ends that include D-shaped extensions 618 (FIG. 24) that are received in the D-shaped bores 616 of the respective first and second toggle members 602 and 604 to rotatably fix the first and second ends of the shaft 606 to the first and second toggle members 602 and 604. The shaft 606 includes a reduced diameter portion 620 that defines a channel 622 (FIG. 24) and an elongated slot 624 that communicates with the channel 622. The safety slider 608 has a circular body 626 and a stop member 628 that extends outwardly from the circular body 626 and includes a tapered cam surface 628a. The circular body 626 of the safety slider 608 is slidably positioned about the reduced diameter portion 620 of the shaft 606 and includes an inwardly extending tab 630 and a protrusion 631 that extends towards the second toggle member 604. The tab 630 extends through the elongated slot 624 into the channel 622 of the shaft 606 to prevent the safety slider 608 from rotating about the shaft 606. The biasing member 610 is positioned between the first toggle member 602 and the tab 630 of the safety slider 608 within the channel 622 of the shaft 606 to urge the safety slider 608 about the reduced diameter portion 620 of the shaft 606 towards the second toggle 604.

The shaft 606 of the safety toggle mechanism 600 supports an arm 632 that extends outwardly from the shaft 606 within the body 340 (FIG. 20) of the handle assembly 312. The shaft 606 is rotatable within the cavity 346 (FIG. 22) of the body 340 (FIG. 1) by rotating the first and second toggle members 602 and 604 from either side of the handle assembly 312 to move the safety toggle mechanism 600 from an inactive position to an active position (FIG. 30). When the safety toggle mechanism 600 is in the active position, the arm 632 is rotated into engagement with a contact 650 (FIG. 30) within the handle assembly 312 to close the contact 650 and place the stapling device 10 (FIG. 1) in a fire-ready position as described in further detail below.

As shown in FIGS. 25 and 26, when the drive assembly of the stapling device 300 (FIG. 1) is in a retracted position, the coupling member 384 is positioned adjacent the stop member 628 of the safety slider 608 to prevent rotation of the safety toggle mechanism 600 from the inactive position to the active position. As such, the stop member 628 prevents the arm 632 on the shaft 606 from moving into engagement with the contact 650 to close the contact 650.

Thus, with the drive assembly of the stapling device 10 (FIG. 1) in the retracted position, the stapling device 300 cannot be fired.

FIGS. 27-31 illustrate the handle assembly 312 as the safety toggle mechanism 600 is moved from the inactive position to the active position. When the drive assembly is moved towards its advanced position to advance the coupling member 384 distally past the stop member 628 of the safety slider 608 and move the tool assembly 316 to the clamped position, the first and second toggle members 602 and 604 can be rotated in the direction of arrows "A" in FIGS. 27 and 29 and 30. When the safety toggle members 602 and 604 are rotated in the direction of arrows "A", the stop member 628 of the safety slider 608 rotates past the coupling member 384 and the arm 632 supported on the shaft 606 moves into engagement with the contact 650 (FIG. 30) to move the contact 650 to a closed position and place the stapling device 300 in a fire-ready position. With the contact 650 closed, the stapling device 300 (FIG. 20) can be actuated by depressing the actuation buttons 320.

Figure 28:
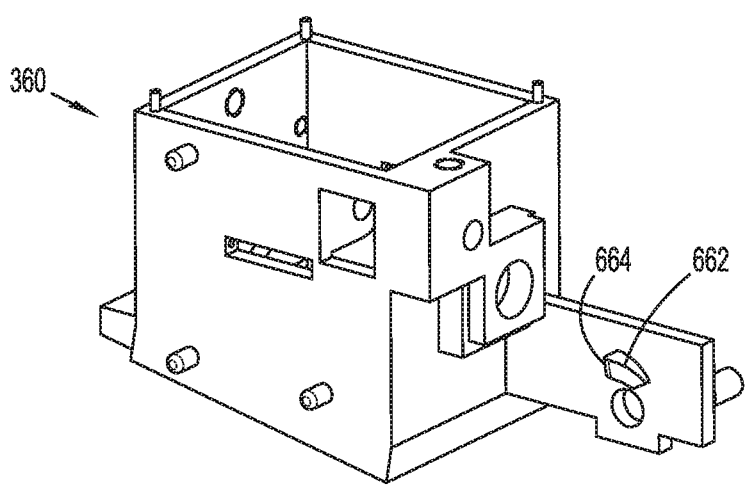
FIG. 28 is a side perspective view of a gear housing of the handle assembly shown in FIG. 21.
Figure 29:
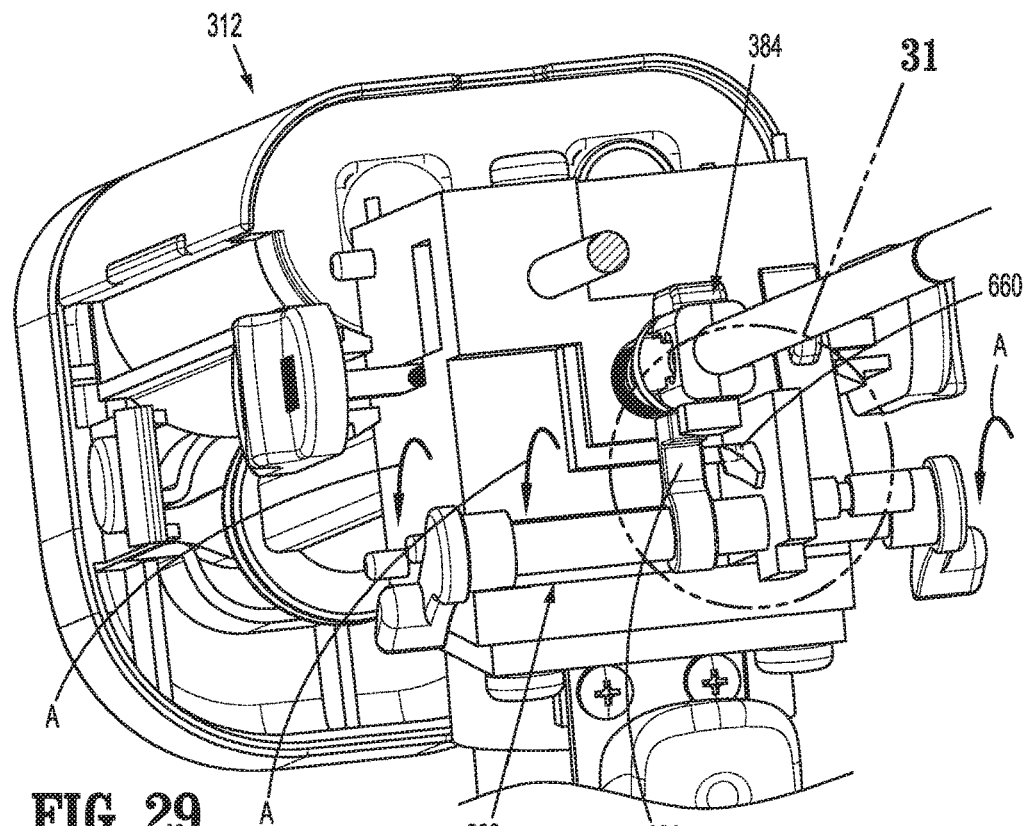
FIG. 29 is a perspective view from the distal end of the handle assembly shown in FIG. 21 with the body half-sections and an articulation linkage of an articulation mechanism of the handle assembly removed with the safety toggle mechanism in the activated position.

As the abutment member 628 of the safety slider 608 moves in the direction of arrow "A", a projection 660 formed on the safety slider 608 engages and moves along a tapered cam member 662 (FIG. 28) formed on the gear housing 360. This engagement cams the safety slider 608 in the direction of arrow "B" in FIG. 27 against the urging of the biasing member 610 along the reduced diameter portion of the shaft 606 past the tapered cam member 662. When the projection 660 moves past the tapered cam member 662, the biasing member 610 returns the safety slider 608 to its original position on the reduced diameter portion 620 of the shaft 606. The tapered cam member 662 has a proximal stop surface 664 (FIG. 28). When the projection 660 passes off of the tapered cam member 662, the projection 660 engages the stop surface 664 on the gear housing 360 to retain the safety toggle mechanism 600 in the active position. As stated above, in the active position, the contact 650 is in a closed position to place the stapling device 300 in a fire-ready position.

The stapling device 300 includes a manual retraction mechanism 710 (FIG. 21) which is substantially like the manual retraction mechanism 210 (FIG. 5) of the handle assembly 12 (FIG. 1) of the surgical stapling device 10 (FIG. 1).

Figure 32:
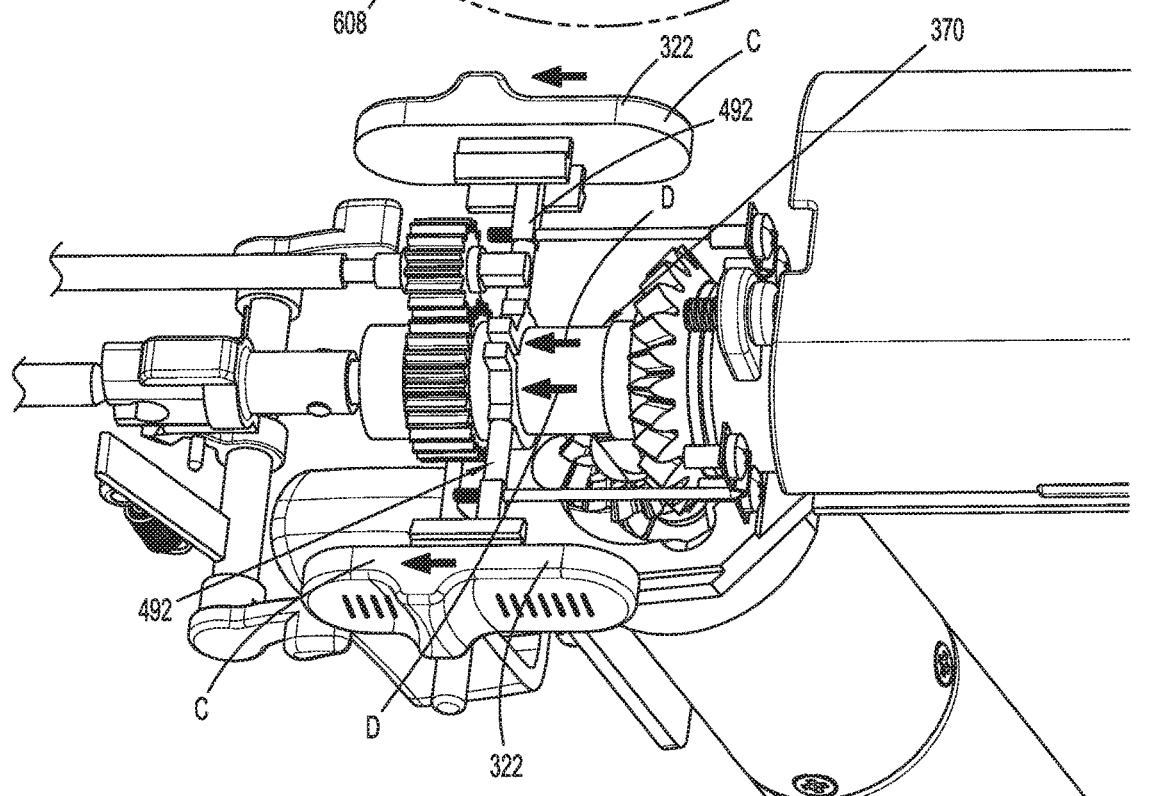
FIG. 32 is a perspective view from above with the body half-sections of the handle assembly shown in FIG. 21 removed and the clutch in an articulation position.

FIG. 32 illustrates the operation of the selector switch assembly 490. As detailed above, the clutch 370 is urged by the biasing member 484 (FIG. 24) (and to a lesser extent by biasing members 520) towards the clamp/fire position. In order to move the clutch 370 to the articulation position, one or both of the clutch switches 322 can be engaged by a clinician and slid distally along the body 340 (FIG. 20) of the handle assembly 312 in the direction of arrows "C" to move the fork members 492 in the direction of arrows "C". The fork members 492 are secured about the clutch 370 such that movement of the fork members 492 in the direction of arrows "C" moves the clutch 370 in the direction of arrows "D" to the articulation position in which the splines 476 (FIG. 24) on the distal portion of the clutch 370 are engaged with the splines 414 (FIG. 23) of the first articulation gear 400. When the selector switch assembly 490 is released by a clinician, the biasing member 484 will urge the clutch 370 back to the clamp/fire position. Operation of the stapling device 300 (FIG. 20) with the clutch 370 in the clamp/fire position and the articulation position is substantially as described above and will not be described in further detail herein.

Persons skilled in the art will understand that the devices and methods specifically described herein and illustrated in the accompanying drawings are non-limiting exemplary aspects of the disclosure. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described aspects of the disclosure. Accordingly, the disclosure is not to be limited by what has been particularly shown and described, except as indicated by the appended claims.

What is claimed is:

1. A handle assembly for a surgical device comprising:
    a housing supporting at least one clutch switch;
    a drive assembly supported within the housing, the drive assembly including a drive screw, a screw nut, and a drive rod, the drive rod having a proximal portion and a distal portion, the screw nut defining a threaded bore and including external splines, the drive screw extending through the threaded bore, and the drive rod having a proximal portion coupled to the drive screw;
    an articulation mechanism supported within the housing, the articulation mechanism including a first articulation gear, a second articulation gear, and an articulation screw, the first articulation gear defining a through bore and including internal splines positioned within the through bore and outer gear teeth, the second articulation gear including outer gear teeth that are engaged with the outer gear teeth of the first articulation gear;
    a clutch supported within the housing between the first articulation gear and the screw nut, the clutch movable between an actuation position in which the clutch is engaged with the external splines of the screw nut for operably actuating the surgical device, and an articulation position in which the clutch is disengaged with the external splines of the screw nut and engaged with the internal splines of the first articulation gear for non-actuating motion of the surgical device;
    a biasing member supported within the housing, the biasing member urging the clutch towards the actuation position;
    a motor coupled to the clutch, the motor operable to rotate the clutch within the housing to actuate one of the drive assembly or the articulation mechanism;
    a safety toggle mechanism supported on the housing, the safety toggle mechanism including at least one toggle member, a shaft coupled to the at least one toggle member, and a slider mounted on the shaft and including a stop member, the shaft being rotatable to move the safety toggle mechanism from an inactive position in which the handle assembly is deactivated to an active position in which the handle assembly is activated; and
    a tapered cam member supported by the housing and having a tapered cam surface and a proximal stop surface, and with the slider having a projection movable along the tapered cam surface to move the slider from a first position on the shaft, in which the slider is aligned with the tapered cam member, to a second position on the shaft in which the slider is positioned outwardly of the tapered cam member as the safety toggle mechanism is moved from the inactive position to the active position;
    wherein, when the safety toggle mechanism is in the active position, the projection is aligned with the proximal stop surface to retain the safety toggle mechanism in the active position.

2. The handle assembly of claim 1, further including a first bevel gear coupled to the motor and a second bevel gear coupled to the first bevel gear.

3. The handle assembly of claim 2, wherein the second bevel gear defines a through bore and a longitudinal slot that communicates with the through bore of the second bevel gear, the through bore of the second bevel gear receiving the screw nut and the drive screw, and the clutch including a raised extension that is received within the longitudinal slot to rotatably couple the clutch to the second bevel gear.

4. The handle assembly of claim 1, wherein the articulation mechanism includes an articulation link that is coupled to the articulation screw such that movement of the articulation screw causes longitudinal movement of the articulation link.

5. The handle assembly of claim 1, wherein the at least one clutch switch includes a clutch switch on each side of the housing, the clutch switches coupled to the clutch by forked members, and the clutch switches movable along the housing to move the clutch from the actuation position to the articulation position.

6. The handle assembly of claim 5, wherein the housing supports guide rods and the forked members define openings, the guide rods extending through the openings in the forked members to guide movement of the forked members as the clutch is moved from the actuation position to the articulation position.

7. The handle assembly of claim 1, wherein the housing of the handle assembly supports a contact and the shaft of the safety toggle mechanism includes an arm, wherein in the inactive position of the safety toggle mechanism, the arm is spaced from the contact and the contact is in an open position, and in the active position of the safety toggle mechanism, the arm is engaged with the contact and the contact is in a closed position.

8. The handle assembly of claim 1, wherein the drive assembly includes a coupling member that couples the drive screw to the drive rod, the drive screw, the coupling member and the drive rod movable between retracted and advanced positions within the housing in response to actuation of the motor when the clutch is in the actuation position.

9. The handle assembly of claim 8, wherein the coupling member is positioned to obstruct movement of the safety toggle mechanism from the inactive position to the active position when the coupling member is in its retracted position.

10. The handle assembly of claim 1, wherein the slider is urged towards the first position by a biasing mechanism.

11. A surgical device comprising:
    a handle assembly including:
        a housing supporting at least one clutch switch;
        a drive assembly supported within the housing, the drive assembly including a drive screw, a screw nut, and a drive rod, the drive rod having a proximal portion and a distal portion, the screw nut defining a threaded bore and including external splines, the drive screw extending through the threaded bore, and the drive rod having a proximal portion coupled to the drive screw;
        an articulation mechanism supported within the housing, the articulation mechanism including a first articulation gear, a second articulation gear, and an articulation screw, the first articulation gear defining a through bore and including internal splines positioned within the through bore and outer gear teeth, the second articulation gear including outer gear teeth that are engaged with the outer gear teeth of the first articulation gear;

a clutch supported within the housing between the first articulation gear and the screw nut, the clutch movable between an actuation position in which the clutch is engaged with the external splines of the screw nut for operably actuating the surgical device, and an articulation position in which the clutch is disengaged with the external splines of the screw nut and engaged with the internal splines of the first articulation gear for non-actuating motion of the surgical device;

a biasing member supported within the housing, the biasing member urging the clutch towards the actuation position;

a motor coupled to the clutch, the motor operable to rotate the clutch within the housing;

a safety toggle mechanism supported on the housing, the safety toggle mechanism including at least one toggle member, a shaft coupled to the at least one toggle member, and a slider mounted on the shaft and including a stop member, the shaft being rotatable to move the safety toggle mechanism from an inactive position in which the handle assembly is deactivated to an active position in which the handle assembly is activated; and a tapered cam member supported by the housing and having a tapered cam surface and a proximal stop surface, and with the slider having a projection movable along the tapered cam surface to move the slider from a first position on the shaft, in which the slider is aligned with the tapered cam member, to a second position on the shaft in which the slider is positioned outwardly of the tapered cam member as the safety toggle mechanism is moved from the inactive position to the active position, wherein, when the safety toggle mechanism is in the active position, the projection is aligned with the proximal stop surface to retain the safety toggle mechanism in the active position;

an adapter assembly defining a longitudinal axis and having a proximal portion and a distal portion, the adapter assembly including an articulation rod, the proximal portion of the adapter assembly coupled to the handle assembly, the articulation rod having a proximal portion coupled to the articulation screw and a distal portion, the drive rod extending through the adapter assembly; and a tool assembly pivotably coupled to the distal portion of the adapter assembly about an axis that is transverse to the longitudinal axis of the adapter assembly, the distal portion of the articulation rod coupled to the tool assembly to pivot the tool assembly between a non-articulated position in which the tool assembly is aligned with the longitudinal axis and articulated positions in which the tool assembly is misaligned with the longitudinal axis.

12. The surgical device of claim 11, wherein the at least one clutch switch includes a clutch switch supported on each side of the housing of the handle assembly, the clutch switches coupled to the clutch and movable along the housing of the handle assembly to move the clutch from the actuation position to the articulation position.

13. The surgical device of claim 11, wherein the housing of the handle assembly supports a contact and the shaft of the safety toggle mechanism includes an arm, wherein in the inactive position of the safety toggle mechanism, the arm is spaced from the contact and the contact is in an open position, and in the active position of the safety toggle mechanism, the arm is engaged with the contact and the contact is in a closed position.

14. The surgical device of claim 13 wherein the drive assembly includes a coupling member that couples the drive screw to the drive rod, the drive screw, the coupling member and the drive rod movable between retracted and advanced positions within the housing in response to actuation of the motor when the clutch is in the actuation position.

15. The surgical device of claim 14, wherein the coupling member is positioned to obstruct movement of the safety toggle mechanism from the inactive position to the active position when the coupling member is in its retracted position.

16. The surgical device of claim 15, wherein the slider is urged towards the first position by a biasing mechanism.

* * * * *